United States Patent
Eshbaugh et al.

(10) Patent No.: US 9,655,530 B2
(45) Date of Patent: May 23, 2017

(54) APPARATUS AND METHODS FOR NON-INVASIVELY MEASURING PHYSIOLOGIC PARAMETERS OF ONE OR MORE SUBJECTS

(75) Inventors: Dave Eshbaugh, Vista, CA (US); Oliver Goedje, Strasslach (DE); Matthias Bohn, Munich (DE)

(73) Assignee: Tensys Medical, Inc., San Diego, CA (US)

( * ) Notice: Subject to any disclaimer, the term of this patent is extended or adjusted under 35 U.S.C. 154(b) by 213 days.

(21) Appl. No.: 13/098,344

(22) Filed: Apr. 29, 2011

(65) Prior Publication Data

US 2012/0277597 A1    Nov. 1, 2012

(51) Int. Cl.
*A61B 5/02* (2006.01)
*A61B 5/021* (2006.01)
*A61B 5/00* (2006.01)

(52) U.S. Cl.
CPC .......... *A61B 5/02141* (2013.01); *A61B 5/684* (2013.01); *A61B 5/6824* (2013.01); *A61B 2560/0406* (2013.01); *A61B 2562/16* (2013.01)

(58) Field of Classification Search
None
See application file for complete search history.

(56) References Cited

U.S. PATENT DOCUMENTS

| | | | |
|---|---|---|---|
| 2,630,914 A | 3/1953 | Bekoff | |
| 2,753,863 A | 7/1956 | Bailey | |
| 3,090,377 A | 5/1963 | Salisbury et al. | |
| 3,095,873 A | 7/1963 | Edmunds | |
| 3,460,123 A | 8/1969 | Jack | |
| 3,535,067 A | 10/1970 | Lesher et al. | |
| 3,640,123 A | 2/1972 | Vogt et al. | |
| 3,704,708 A | 12/1972 | Iberall | |
| 3,727,250 A | 4/1973 | Koehn et al. | |
| 3,935,984 A | 2/1976 | Lichowsky et al. | |

(Continued)

FOREIGN PATENT DOCUMENTS

CN    101896117 A    11/2010
CN    201664313 U    12/2010

(Continued)

OTHER PUBLICATIONS

Extended European Search Report for Application No. EP07836141, mailed on Nov. 3, 2010, 10 pages.

(Continued)

*Primary Examiner* — Patricia Mallari
*Assistant Examiner* — Mitchelle E Alter
(74) *Attorney, Agent, or Firm* — Gazdzinski & Associates, PC

(57) ABSTRACT

Improved apparatus and methods for non-invasively assessing one or more physiologic (e.g., hemodynamic) parameters associated with a living organism. In one embodiment, the invention comprises an apparatus adapted to automatically and accurately place and maintain a sensor (e.g., tonometric pressure sensor) with respect to the anatomy of the subject. The apparatus is comprised of a sensor device removably coupled to a host device which is used to position the sensor during measurements. Methods for positioning the alignment apparatus and sensor, and operating the apparatus, are also disclosed.

26 Claims, 18 Drawing Sheets

(56) References Cited

U.S. PATENT DOCUMENTS

| | | |
|---|---|---|
| 4,206,765 A | 6/1980 | Huber |
| 4,274,424 A | 6/1981 | Kimura et al. |
| 4,380,240 A | 4/1983 | Jobsis et al. |
| 4,406,289 A | 9/1983 | Wesseling et al. |
| 4,441,504 A | 4/1984 | Peterson et al. |
| 4,595,023 A | 6/1986 | Bonnet |
| 4,867,170 A | 9/1989 | Takahashi |
| 4,924,871 A | 5/1990 | Honeyager |
| 4,993,422 A | 2/1991 | Hon et al. |
| 4,998,534 A | 3/1991 | Claxton, III et al. |
| 5,072,733 A | 12/1991 | Spector et al. |
| 5,240,007 A | 8/1993 | Pytel et al. |
| 5,261,412 A | 11/1993 | Butterfield et al. |
| 5,271,405 A | 12/1993 | Boyer et al. |
| 5,284,150 A | 2/1994 | Butterfield et al. |
| 5,313,952 A | 5/1994 | Hoch |
| 5,351,694 A | 10/1994 | Davis et al. |
| 5,450,852 A | 9/1995 | Archibald et al. |
| 5,617,867 A | 4/1997 | Butterfield et al. |
| 5,630,914 A | 5/1997 | Sachdeva et al. |
| 5,640,964 A | 6/1997 | Archibald et al. |
| 5,642,733 A | 7/1997 | Archibald et al. |
| 5,649,542 A | 7/1997 | Archibald et al. |
| 5,722,414 A | 3/1998 | Archibald et al. |
| 5,762,610 A | 6/1998 | Narimatsu et al. |
| 5,832,924 A | 11/1998 | Archibald et al. |
| 5,908,027 A | 6/1999 | Butterfield et al. |
| 5,938,618 A | 8/1999 | Archibald et al. |
| 5,941,828 A | 8/1999 | Archibald et al. |
| 6,099,477 A | 8/2000 | Archibald et al. |
| 6,132,382 A | 10/2000 | Archibald et al. |
| 6,132,383 A | 10/2000 | Chesney et al. |
| 6,159,157 A | 12/2000 | Archibald et al. |
| 6,176,831 B1 | 1/2001 | Voss et al. |
| 6,176,931 B1 | 1/2001 | Restaino et al. |
| 6,228,034 B1 | 5/2001 | Voss et al. |
| 6,241,679 B1 | 6/2001 | Curran |
| 6,245,022 B1 | 6/2001 | Archibald et al. |
| 6,290,650 B1 | 9/2001 | Butterfield et al. |
| 6,313,729 B1 | 11/2001 | Winterer et al. |
| 6,340,349 B1 | 1/2002 | Archibald et al. |
| 6,390,985 B1 | 5/2002 | Mamayek |
| D458,375 S | 6/2002 | Thede |
| 6,471,655 B1 | 10/2002 | Baura |
| 6,520,920 B2 | 2/2003 | Nissila et al. |
| 6,544,188 B1 | 4/2003 | Chesney |
| 6,554,774 B1 | 4/2003 | Miele |
| 6,558,335 B1 | 5/2003 | Thede |
| 6,676,600 B1 | 1/2004 | Conero |
| 6,695,789 B2 | 2/2004 | Thede et al. |
| 6,730,038 B2 | 5/2004 | Gallant et al. |
| 6,733,462 B1 | 5/2004 | Frick et al. |
| 6,869,254 B1 | 3/2005 | Kershman |
| 6,974,419 B1 | 12/2005 | Voss et al. |
| 7,048,691 B2 | 5/2006 | Miele et al. |
| 7,163,877 B2 | 1/2007 | Niimi et al. |
| 7,291,112 B2 | 11/2007 | Martin et al. |
| 7,317,409 B2 | 1/2008 | Conero |
| 7,503,896 B2 | 3/2009 | Miele et al. |
| 7,946,994 B2 | 5/2011 | Finburgh et al. |
| 2001/0039383 A1 | 11/2001 | Mohler |
| 2002/0026121 A1 | 2/2002 | Kan |
| 2002/0055680 A1 | 5/2002 | Miele et al. |
| 2002/0062086 A1 | 5/2002 | Miele et al. |
| 2002/0125164 A1 | 9/2002 | Bassinson |
| 2002/0133210 A1 | 9/2002 | Gruzdowich et al. |
| 2002/0138136 A1 | 9/2002 | Chandresekaran |
| 2003/0141916 A1 | 7/2003 | Conero |
| 2003/0149369 A1* | 8/2003 | Gallant et al. ............... 600/485 |
| 2003/0153824 A1 | 8/2003 | Tsubata |
| 2004/0073123 A1 | 4/2004 | Hessel et al. |
| 2005/0070837 A1 | 3/2005 | Ferrarini et al. |
| 2005/0080345 A1 | 4/2005 | Finburgh et al. |
| 2006/0079792 A1 | 4/2006 | Finburgh et al. |
| 2006/0135896 A1* | 6/2006 | Latimer ........................ 602/2 |
| 2006/0184051 A1 | 8/2006 | Hempstead et al. |
| 2007/0021674 A1 | 1/2007 | Thede et al. |
| 2008/0021334 A1* | 1/2008 | Finburgh et al. ............ 600/490 |
| 2009/0131806 A1* | 5/2009 | Finburgh et al. ............ 600/485 |
| 2011/0009723 A1* | 1/2011 | Mannheimer et al. ....... 600/324 |

FOREIGN PATENT DOCUMENTS

| | | |
|---|---|---|
| EP | 0 818 176 | 1/1998 |
| JP | 2003325463 A | 11/2003 |
| JP | 2009543664 A | 12/2009 |
| WO | WO-9625087 A1 | 8/1996 |
| WO | WO-0100087 A1 | 1/2001 |

OTHER PUBLICATIONS

"Extended European Search Report for Application No. EP08838390, mailed on Oct. 18, 2013, 8 pages".

International Preliminary Report on Patentabilit for Application No. PCT/US2008/011629, mailed on Apr. 13, 2010, 6 pages.

International Search Report and Written Opinion for Application No. PCT/US2008/011629, mailed on Jan. 15, 2009, 6 pages.

Office Action mailed Apr. 30, 2015 for Indian Application No. 1715/KOLNP/2010 filed Dec. 12, 2010, 2 pages.

Office Action mailed Mar. 31, 2013 for Chinese Application No. 201280008439.8 filed Apr. 27, 2012, 20 pages.

Supplementary European Search Report for Application No. EP03776272, mailed on Feb. 19, 2008, 5 pages.

* cited by examiner

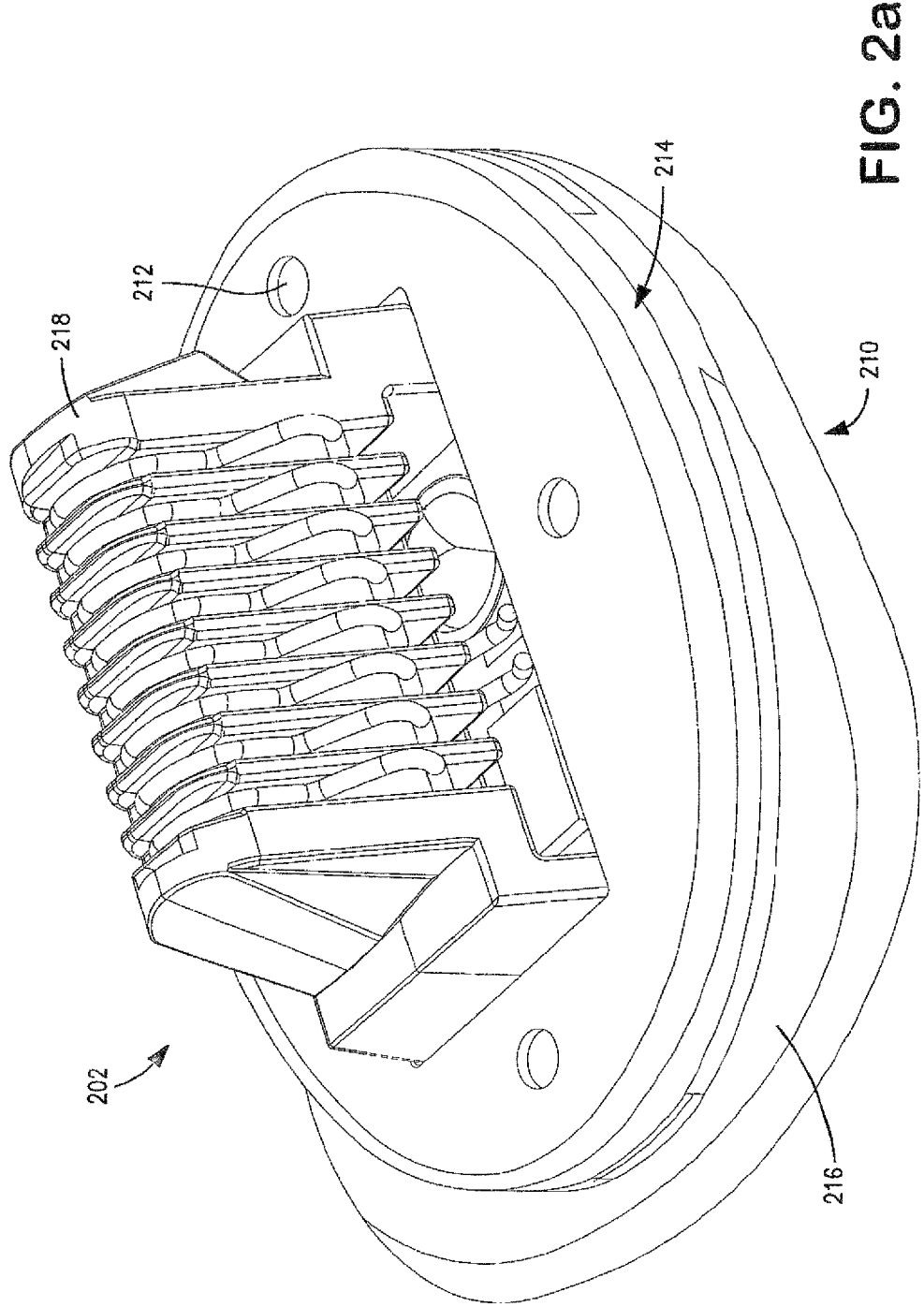

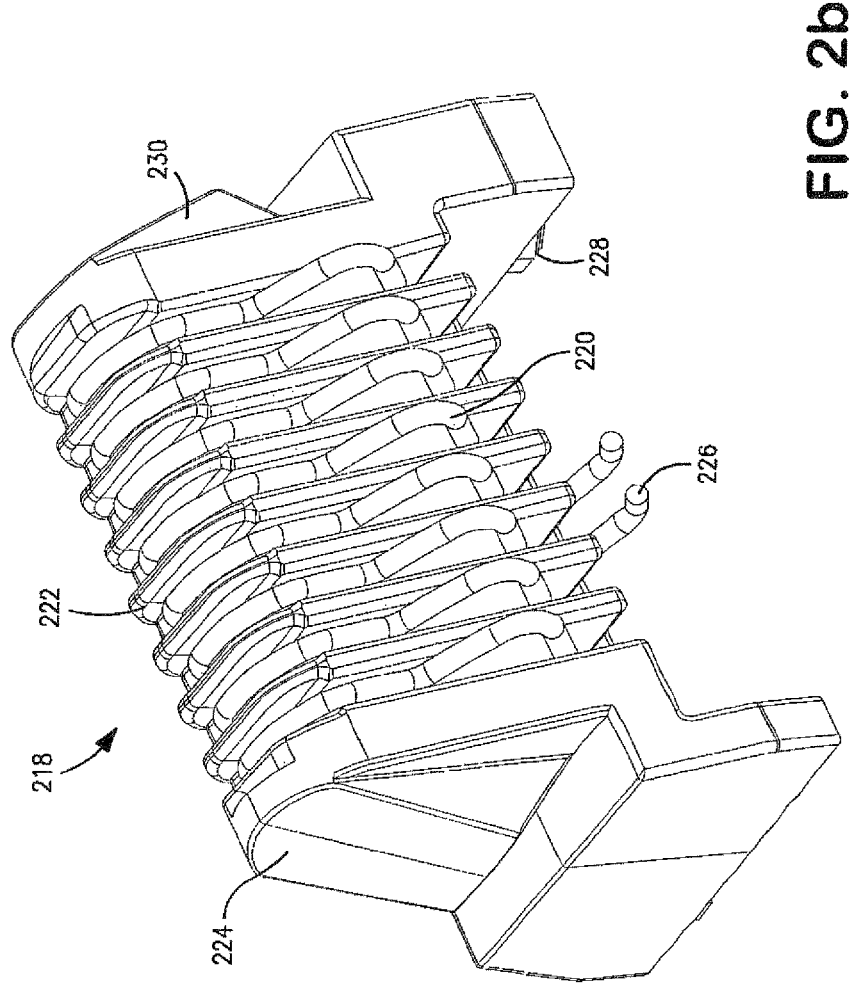

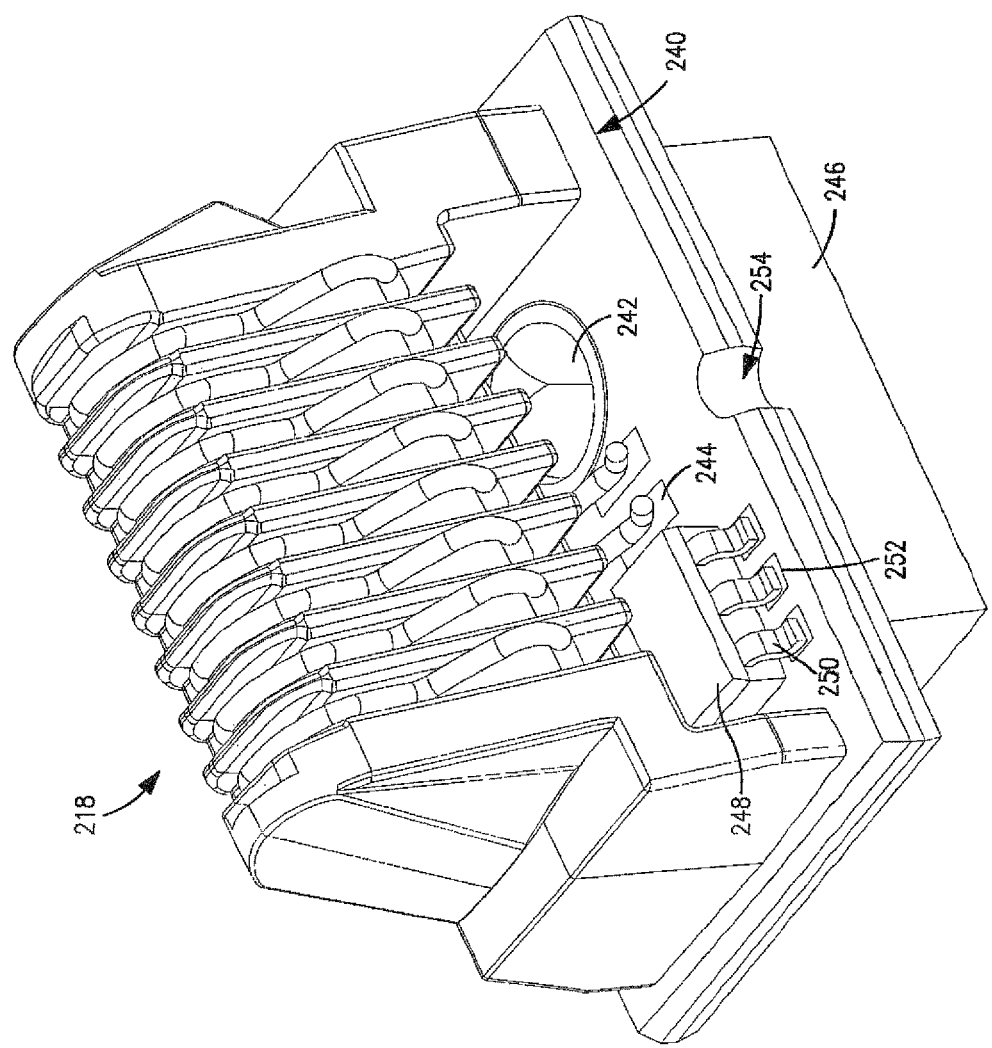

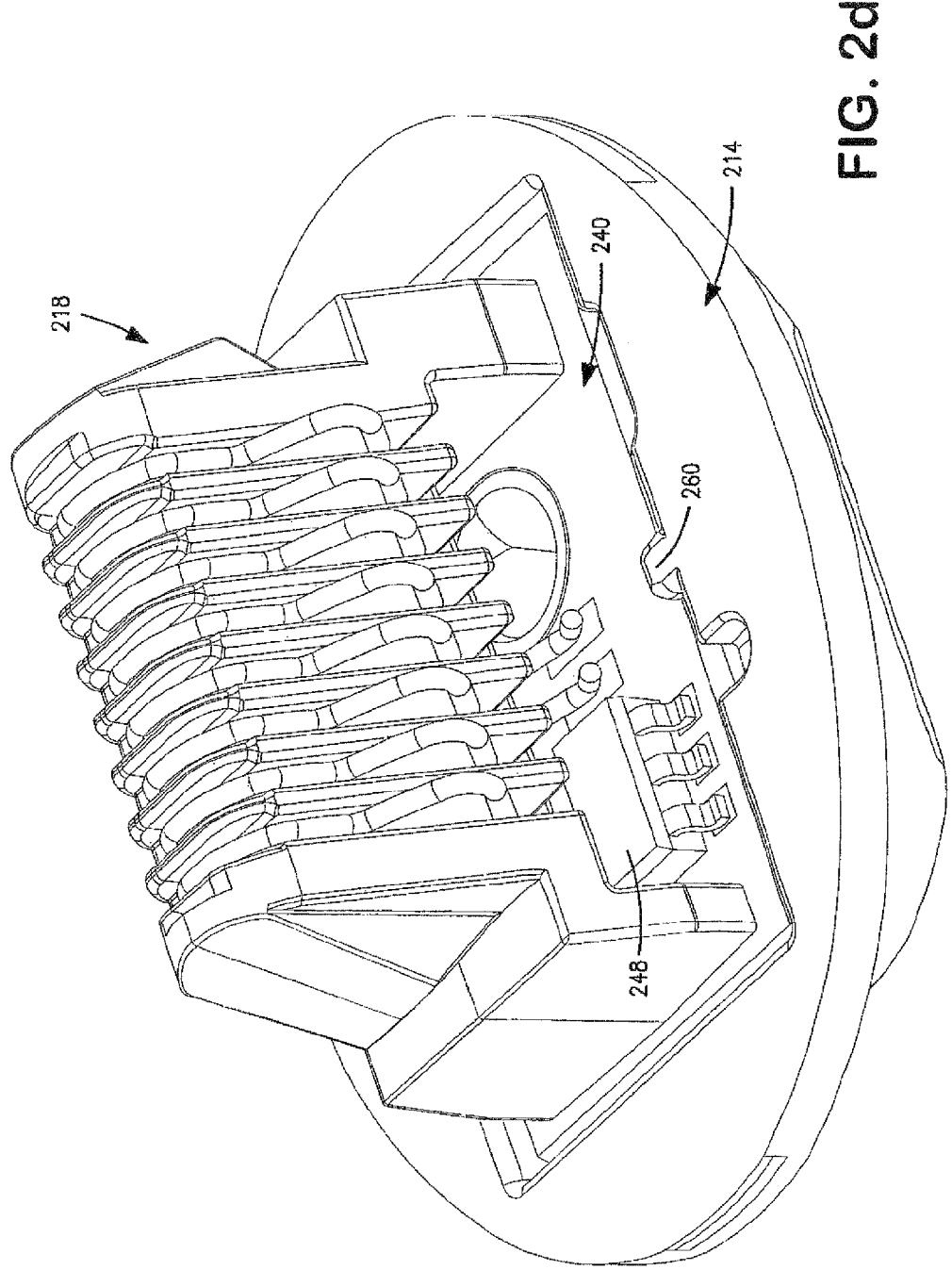

APPARATUS AND METHODS FOR NON-INVASIVELY MEASURING PHYSIOLOGIC PARAMETERS OF ONE OR MORE SUBJECTS

RELATED APPLICATIONS

This application is related to U.S. Patent Application Publication No. 2009/0131806 entitled "Apparatus and Methods for Non-Invasively Measuring a Patient's Arterial Blood Pressure" and filed on Oct. 9, 2008 which claims priority to U.S. Provisional Patent Application Ser. No. 60/998,632 filed Oct. 12, 2007 of the same title, each of which is incorporated herein by reference in its entirety. This application is also related to U.S. Patent Application Publication No. 2008/0021334 filed on Jul. 19, 2006 and entitled "Apparatus and Methods for Non-Invasively Measuring Hemodynamic Parameters", and U.S. Patent Application Publication No. 2006/0184051 filed Jan. 20, 2006 entitled "Apparatus and Methods for Non-Invasively Measuring Hemodynamic Parameters" and U.S. Patent Application Publication No. 2005/0080345 filed Aug. 18, 2004 entitled "Apparatus and Methods for Non-Invasively Measuring Hemodynamic Parameters", which are continuation-in-parts of, and claim priority to, U.S. patent application Ser. No. 10/269,801 filed Oct. 11, 2002 all of the same title, and all of foregoing which are incorporated herein by reference in their entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

1. Field of the Invention

This invention relates generally to methods and apparatus for monitoring parameters associated with physiological and fluid systems, and specifically in one aspect to the non-invasive monitoring of arterial blood pressure or other hemodynamic parameters in a living subject.

2. Description of Related Art

The accurate measurement of physiological parameters from a living subject has long been sought by medical science. One such area of particular importance is the non-invasive, continuous measurement of blood pressure and/or other hemodynamic parameters. The availability of such measurement techniques would allow the caregiver to continuously monitor a subject's parameters (e.g., blood pressure) accurately and in repeatable fashion without the use of invasive arterial catheters (commonly known as "A-lines") in any number of settings including, for example, surgical operating rooms where continuous, accurate indications of true blood pressure are often essential.

Several well known techniques have heretofore been used to non-invasively monitor a subject's arterial blood pressure waveform, namely, auscultation, oscillometry, and tonometry. Both the auscultation and oscillometry techniques use a standard inflatable arm cuff that occludes the subject's brachial artery. The auscultatory technique determines the subject's systolic and diastolic pressures by monitoring certain Korotkoff sounds that occur as the cuff is slowly deflated. The oscillometric technique, on the other hand, determines these pressures, as well as the subject's mean pressure, by measuring actual pressure changes that occur in the cuff as the cuff is deflated. Both techniques determine pressure values only intermittently, because of the need to alternately inflate and deflate the cuff, and they cannot replicate the subject's actual blood pressure waveform. Thus, true continuous, beat-to-beat blood pressure monitoring cannot be achieved using these techniques.

Occlusive cuff instruments of the kind described briefly above have generally been somewhat effective in sensing long-term trends in a subject's blood pressure. However, such instruments generally have been ineffective in sensing short-term blood pressure variations, which are of critical importance in many medical applications, including surgery.

The technique of arterial tonometry is also well known in the medical arts. According to the theory of arterial tonometry, the pressure in a superficial artery with sufficient bony support, such as the radial artery, may be accurately recorded during an applanation sweep when the transmural pressure equals zero. The term "applanation" refers generally to the process of varying the pressure applied to the artery. An applanation sweep refers to a time period during which pressure over the artery is varied from overcompression to undercompression or vice versa. At the onset of a decreasing applanation sweep, the artery is overcompressed into a "dog bone" shape, so that pressure pulses are not recorded. At the end of the sweep, the artery is undercompressed, so that minimum amplitude pressure pulses are recorded. Within the sweep, it is assumed that an applanation occurs during which the arterial wall tension is parallel to the tonometer surface. Here, the arterial pressure is perpendicular to the surface and is the only stress detected by the tonometer sensor. At this pressure, it is assumed that the maximum peak-to-peak amplitude (the "maximum pulsatile") pressure obtained corresponds to zero transmural pressure.

One prior art device for implementing the tonometry technique includes a rigid array of miniature pressure transducers that is applied against the tissue overlying a peripheral artery, e.g., the radial artery. The transducers each directly sense the mechanical forces in the underlying subject tissue, and each is sized to cover only a fraction of the underlying artery. The array is urged against the tissue, to applanate the underlying artery and thereby cause beat-to-beat pressure variations within the artery to be coupled through the tissue to at least some of the transducers. An array of different transducers is used to ensure that at least one transducer is always over the artery, regardless of array position on the subject. This type of tonometer, however, is subject to several drawbacks. First, the array of discrete transducers generally is not anatomically compatible with the continuous contours of the subject's tissue overlying the artery being sensed. This has historically led to inaccuracies in the resulting transducer signals. In addition, in some cases, this incompatibility can cause tissue injury and nerve damage and can restrict blood flow to distal tissue.

Other prior art techniques have sought to more accurately place a single tonometric sensor laterally above the artery, thereby more completely coupling the sensor to the pressure variations within the artery. However, such systems may place the sensor at a location where it is geometrically "centered" but not optimally positioned for signal coupling, and further typically require comparatively frequent re-calibration or repositioning due to movement of the subject during measurement. Additionally, the methodology for proper initial and follow-on placement is awkward, essentially relying on the caregiver to manually locate the optimal location for sensor placement on the subject each time, and then mark that location (such as by keeping their finger on the spot, or alternatively marking it with a pen or other marking instrument), after which the sensor is placed over the mark. Alternatively, some prior art techniques rely on additional sensing elements and associated apparatus for positioning the sensor. Utilization of additional apparatus results in increased costs and additional steps for implementing the technology.

Prior art tonometry systems are also commonly quite sensitive to the orientation of the pressure transducer on the subject being monitored. Specifically, such systems show degradation in accuracy when the angular relationship between the transducer and the artery is varied from an "optimal" incidence angle. This is an important consideration, since no two measurements are likely to have the device placed or maintained at precisely the same angle with respect to the artery. Many of the foregoing approaches similarly suffer from not being able to maintain a constant angular relationship with the artery regardless of lateral position, due in many cases to positioning mechanisms which are not adapted to account for the anatomic features of the subject, such as curvature of the wrist surface.

Another deficiency of prior art non-invasive hemodynamic measurement technology relates to the lack of disposability of components associated with the device. Specifically, it is desirable to make portions of the device which may (i) be contaminated in any fashion through direct or indirect contact with the subject(s) being monitored); (ii) be specifically calibrated or adapted for use on that subject; (iii) lose calibration through normal use, thereby necessitating a more involved recalibration process (as opposed to simply replacing the component with an unused, calibrated counterpart), or (iv) disposable after one or a limited number of uses. This feature is often frustrated in prior art systems based on a lack of easy replacement of certain components (i.e., the components were not made replaceable during the design process), or a prohibitively high cost associated with replacing components that are replaceable. Ideally, certain components associated with a non-invasive hemodynamic assessment device would be readily disposable and replaced at a very low cost to the operator.

Yet another disability of the prior art concerns the ability to conduct multiple hemodynamic measurements on a subject at different times and/or different locations. For example, where blood pressure measurements are required in first and second locations (e.g., the operating room and recovery room of a hospital), prior art methodologies necessitate either (i) the use of an invasive catheter (A-line), (ii) transport of the entire blood pressure monitoring system between the locations, or (iii) disconnection of the subject at the first monitoring location, transport, and then subsequent connection to a second blood pressure monitoring system at the second location.

The disabilities associated with invasive catheters are well understood. These include the need to perforate the subject's skin (with attendant risk of infection), and discomfort to the subject.

Transport of the entire blood pressure monitoring system is largely untenable, due to the bulk of the system and the desire to maintain monitoring equipment indigenous to specific locations.

Disconnection and subsequent reconnection of the subject is also undesirable, since it requires placing a sensor or apparatus on the patient's anatomy a second time, thereby necessitating recalibration, and reducing the level of confidence that the measurements taken at the two different locations are in fact directly comparable to one another. Specifically, since the sensor and supporting apparatus is physically withdrawn at the first location, and then a new sensor subsequently placed again on the subject's tissue at the second location, the likelihood of having different coupling between the sensor and the underlying blood vessel at the two locations is significant. Hence, identical intravascular pressure values may be reflected as two different values at the different locations due to changes in coupling, calibration, sensor parameters, and related factors, thereby reducing the repeatability and confidence level associated the two readings.

Additionally, in the prior art, the sensor is often electrically connected to an actuator or other host device via an external electrical connection via a cable or "pigtail". Such connection apparatus adds additional costs and complexity to the system.

Based on the foregoing, there is a need for an improved apparatus and methodology for accurately, continuously, and non-invasively measuring parameters (such as for example those associated with the hemodynamic system) associated with a living subject. Such improved apparatus and methodology would ideally allow for prompt and accurate initial placement of the sensor(s) (e.g., a tonometric pressure sensor, ultrasonic sensor, etc.) without requiring additional alignment apparatus or elements, while also providing robustness and repeatability of placement under varying patient physiology and environmental conditions. Such apparatus would also incorporate low-cost and disposable components.

Such apparatus and methods would furthermore be substantially self-aligning and calibrating (i.e., automatically place itself and "zero" itself) with respect to a patient. Ease of use would also be considered.

SUMMARY OF THE INVENTION

The present invention satisfies the aforementioned needs by an improved apparatus and methods for non-invasively and continuously assessing hemodynamic properties, including arterial blood pressure, within a living subject.

In a first aspect of the invention, a frame assembly for use with a physiologic parameter sensing apparatus is disclosed. In one embodiment, the frame assembly comprises: a substantially conformal frame comprising: at least one aperture for receiving at least an active surface of a sensor; and at least one mating element for mating the sensing apparatus to the frame assembly, the apparatus having the sensor; and a substantially transparent membrane disposed proximate the frame and substantially traversing the aperture.

In a second aspect of the invention, a physiologic parameter sensing apparatus is disclosed. In one embodiment, the apparatus comprises: an alignment element having an optical alignment guide and a sensor barrier; a sensor; and a host device configured to place the sensor relative to the barrier. The sensor barrier is configured to permit sensing of one or more physiologic parameters through the barrier.

In another embodiment, the sensing apparatus comprises: an alignment element having a sensor barrier, the sensor barrier comprising a film configured to permit sensing of one or more physiologic parameters from the skin of the living subject through the barrier; a multi-use sensor; and a host device configured to place the sensor relative to the barrier. The alignment element is configured to be disposed of after a single use, and replaced, and the sensor is configured for multiple uses.

In a third aspect of the invention, a method of measuring one or more physiologic parameters of a living subject is disclosed. In one embodiment, the method comprises: disposing at least one frame element on the subject; mating a host device having a sensor coupled thereto to the frame element, the mating comprising enabling at least an active surface of the sensor to be disposed within an aperture of the frame element; using the host device to automatically position the sensor element at a prescribed monitoring location, and calibrate the sensor element; and measuring the one or more parameters of the subject using the sensor element. The measuring is performed through a membrane which substantially inhibits the sensor from contact with a surface of the subject's skin.

In a fourth aspect, a method of obtaining parametric measurements from a living subject is disclosed. In one embodiment, the method comprises: disposing a support element on the anatomy of the subject, the support element comprising a membrane; disposing a host device having a sensor on the anatomy and in communication with the support element so that sensor is substantially proximate the membrane; and obtaining a parametric measurement through the membrane using the sensor.

In a fifth aspect of the invention, a support element configured to mate with the physiology of a living subject is disclosed. In one embodiment, the support element substantially positions a sensor relative to the subject, and comprises: an at least partly flexible frame configured to substantially conform to a shape of a portion of the physiology; a first element; and a second element having an adhesive disposed on at least a portion thereof. The first element is substantially sandwiched between the frame and the second element; and the adhesive of the second element is useful for removably bonding the support element to the portion of the physiology.

In a sixth aspect of the invention, a method of measuring hemodynamic parameters using a multi-use sensor and single use sensor frame is disclosed.

In a seventh aspect of the invention, a multi-use sensor having a removable protective cover is disclosed.

In an eighth aspect of the invention, a single-use frame element having a protective membrane for maintaining separation of the subject's skin and the active surface of a multi-use sensor is disclosed.

These and other features of the invention will become apparent from the following description of the invention, taken in conjunction with the accompanying drawings.

BRIEF DESCRIPTION OF THE DRAWINGS

FIG. 2a is an illustration of one exemplary embodiment of the fully encapsulated sensor connector assembly.

FIG. 2b is an illustration of the sensor connector of the exemplary embodiment of the sensor connector assembly of FIG. 2a.

FIG. 2c is an illustration of the sensor connector of the exemplary embodiment of the sensor connector assembly mounted on a printed circuit board with a pressure sensor and a storage device (e.g., EEPROM).

FIG. 2d is an illustration of the sensor connector, pressure sensor and EEPROM of the exemplary embodiment of the sensor connector assembly mounted on a printed circuit board and placed in the connector housing.

FIG. 2i is a perspective exploded view of a reusable sensor element assembly according to one embodiment of the invention.

FIG. 3a is a cross-sectional view of the mated actuator and sensor assembly of FIG. 3a.

FIG. 3b is a break-away view of the mated actuator and sensor assembly of FIG. 3a.

DETAILED DESCRIPTION OF THE INVENTION

Figure 1:
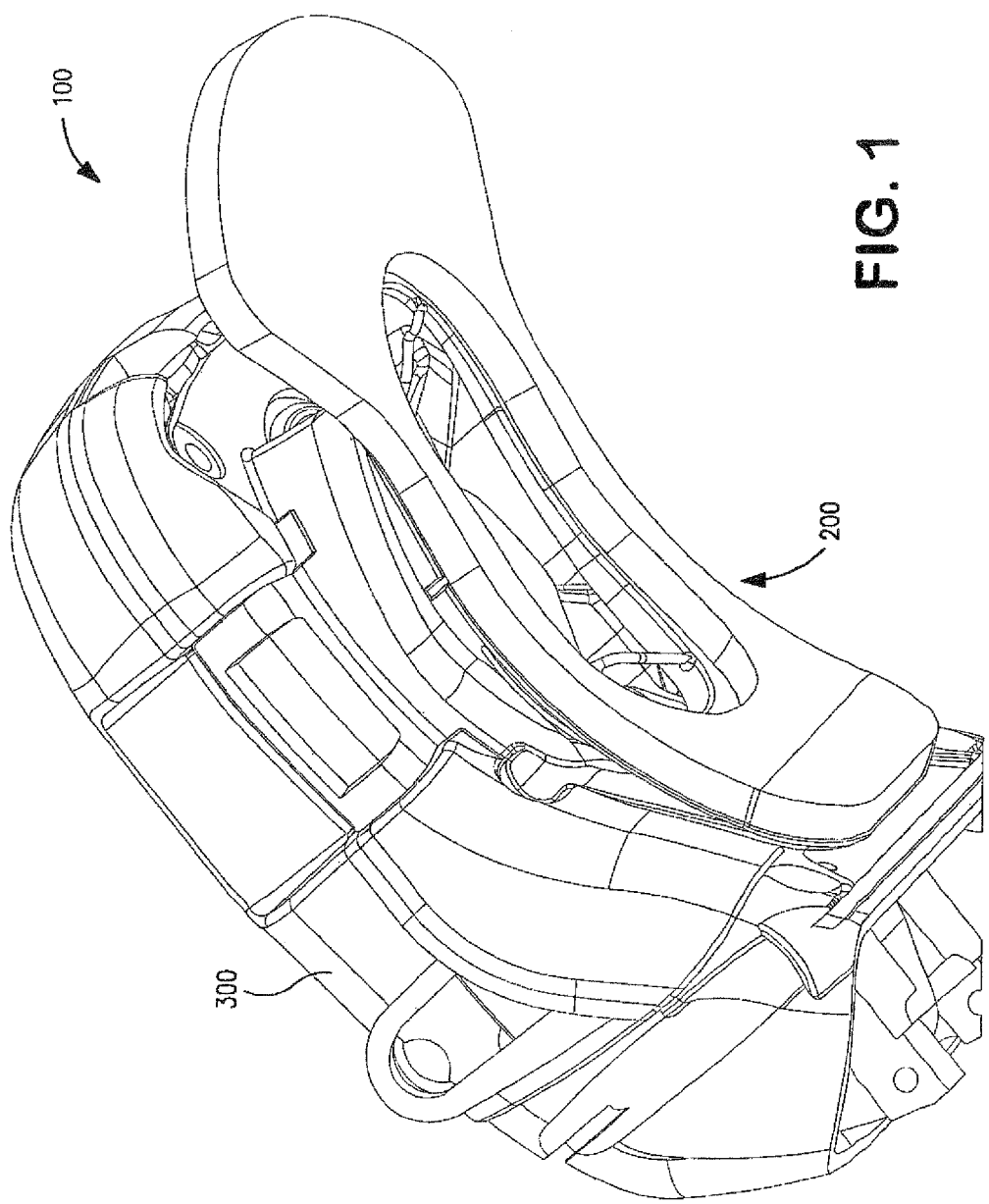
FIG. 1 is a bottom perspective view of one exemplary embodiment of the hemodynamic assessment apparatus of the present invention, shown with sensor assembly coupled to the top portion of the actuator assembly.

Reference is now made to the drawings wherein like numerals refer to like parts throughout.

It is noted that while the invention is described herein primarily in terms of a method and apparatus for assessment of hemodynamic parameters of the circulatory system via the radial artery (i.e., wrist or forearm) of a human subject, the invention may also be readily embodied or adapted to monitor such parameters at other blood vessels and locations on the human body, as well as monitoring these parameters on other warm-blooded species. All such adaptations and alternate embodiments are readily implemented by those of ordinary skill in the relevant arts, and are considered to fall within the scope of the claims appended hereto.

As used herein, the term "hemodynamic parameter" is meant to include parameters associated with the circulatory system of the subject, including for example pressure (e.g., diastolic, systolic, pulse, or mean), blood flow kinetic energy, velocity, density, time-frequency distribution, the presence of stenoses, $SpO_2$, pulse period, as well as any artifacts relating to the pressure waveform of the subject.

Additionally, it is noted that the terms "tonometric," "tonometer," and "tonometry" as used herein are intended to broadly refer to non-invasive surface measurement of one or more hemodynamic parameters such as pressure, such as by placing a sensor in communication with the surface of the skin, although contact with the skin need not be direct (e.g., such as through a coupling medium or other interface).

The terms "applanate" and "applanation" as used herein refer to the compression (relative to a state of non-compression) of tissue, blood vessel(s), and other structures such as tendon or muscle of the subject's physiology. Similarly, an applanation "sweep" refers to one or more periods of time during which the applanation level is varied (either increasingly, decreasingly, or any combination thereof). Although generally used in the context of linear (constant velocity) position variations, the term "applanation" as used herein may conceivably take on any variety of other forms, including without limitation (i) a continuous non-linear (e.g., logarithmic) increasing or decreasing compression over time; (ii) a non-continuous or piece-wise continuous linear or non-linear compression; (iii) alternating compression and relaxation; (iv) sinusoidal or triangular waves functions; (v) random motion (such as a "random walk"); or (vi) a deterministic profile. All such forms are considered to be encompassed by the term.

As used herein, the term "integrated circuit (IC)" refers to any type of device having any level of integration (including without limitation ULSI, VLSI, and LSI) and irrespective of process or base materials (including, without limitation Si, SiGe, CMOS and GaAs). ICs may include, for example, memory devices (e.g., DRAM, SRAM, DDRAM, EEPROM/Flash, ROM), digital processors, SoC devices, FPGAs, ASICs, ADCs, DACs, transceivers, memory controllers, and other devices, as well as any combinations thereof.

As used herein, the term "memory" includes any type of integrated circuit or other storage device adapted for storing digital data including, without limitation, ROM. PROM, EEPROM, DRAM, SDRAM, DDR/2 SDRAM, EDO/FPMS, RLDRAM, SRAM, "flash" memory (e.g., NAND/NOR), and PSRAM.

Overview

In one fundamental aspect, the present invention comprises apparatus and associated methods for accurately and repeatably (if desired) disposing one or more sensors with respect to the anatomy of a subject to facilitate physiologic parameter measurements using the sensor(s). For example, as will be described in greater detail below, the present invention is useful for accurately placing a pressure sensor assembly for continuously and non-invasively measuring the blood pressure or other parameters from the radial artery of a human being. However, literally any kind of sensor (ultrasound, optical, etc.) can be used alone or in combination consistent with the invention, including for example the devices and associated techniques described in co-pending U.S. patent application Ser. No. 10/961,460 entitled "Compact Apparatus and Methods For Non-Invasively Measuring Hemodynamic Parameters" filed Oct. 7, 2004, Ser. No. 09/815,982 entitled "Method and Apparatus for the Noninvasive Assessment of Hemodynamic Parameters Including Blood Vessel Location" filed Mar. 22, 2001, and Ser. No. 09/815,080 entitled "Method and Apparatus for Assessing Hemodynamic Parameters within the Circulatory System of a Living Subject", now U.S. Pat. No. 7,048,691, each of which are assigned to the assignee hereof and incorporated herein by reference in their entirety.

In one exemplary embodiment, the aforementioned pressure sensor is coupled to an actuator mechanism carried by a brace or "bracelet" assembly worn by the subject in the area of the radial artery. The actuator mechanism, when coupled to the sensor, controls the sensor lateral (and proximal, if desired) position as well as the level of applanation of the underlying tissue according to any number of control schemes, including for example that set forth in Assignee's co-pending U.S. patent application Ser. No. 10/211,115 filed Aug. 1, 2002, entitled "Method and Apparatus for Control of Non-Invasive Parameter Measurements", now U.S. Pat. No. 6,974,419, and in co-pending application Ser. No. 10/072,508 filed Feb. 5, 2002, entitled "Method and Apparatus for Non-Invasively Measuring Hemodynamic Parameters Using Parametrics," now U.S. Pat. No. 6,730,038, both of which are incorporated herein by reference in their entirety. However, the present invention is also compatible with systems having separate sensor(s) and applanation mechanisms, as well as combinations of the foregoing features and sensors. The actuator is advantageously "displacement" driven, and accordingly does not rely on measurements of applied force, but rather merely displacement. This approach greatly simplifies the construction and operation of the actuator (and parent control system) by obviating force sensors and signal processing relating thereto, and further makes the actuator and system more robust.

The apparatus of the present invention also advantageously maintains a highly rigid coupling between the sensor assembly and the bracelet element (actuator) used to receive the subject's anatomy, thereby further enhancing the accuracy of the system through elimination of nearly all compliance within the apparatus.

In another aspect, the present invention is superior to the prior art in that it incorporates automatic zeroing of the sensor. The automatic zeroing capability permits the sensor connector assembly to be positioned without the use of additional elements thereby supporting efficient placement of the sensor.

Another significant feature of the exemplary embodiment of the present invention is that it incorporates electrical circuitry directly on the sensor so as to facilitate simplified assembly, operation and calibration of the assembly.

Other significant features of the present invention include (i) ease of use under a variety of different operational environments; (ii) repeatability of measurements; and (iii) disposability of certain components. These features are achieved through the use of novel structures and techniques for placing the sensor(s) and operating the device, as well as significant modularity in design and consideration of the constraints relating to the typical (and atypical) clinical environment.

In one aspect, the present invention overcomes the disabilities associated with the prior art by providing a sensor assembly which is detachable from the parent apparatus and remains positioned on the subject during transport, thereby facilitating highly repeatable measurements using the same sensor at different physical locations within the care facility (e.g., hospital), as described in Assignee's co-pending U.S. patent application Ser. No. 11/336,222 filed Jan. 20, 2006 entitled "Apparatus and methods for non-invasively measuring hemodynamic parameters" which Assignee hereby incorporates by reference in its entirety. The abovementioned features and other features are now described in detail.

In yet another aspect of the invention, hemodynamic parameter measurements are obtained using an apparatus comprising a sensor that senses one or more parameters from the subject(s) through a protective barrier or film. In one such variant, the sensor is designed for multiple uses (i.e., is reusable), and the supporting element and film barrier is limited use (e.g., one-time use). The disposable frame element with barrier is placed on the surface of the subject's skin, and thereby insulating or protecting the face of the sensor element from contact with the skin. This configuration ensures that the sensor face remains clean for multiple uses, even across several different subjects. The sensor mates to an actuator device, which adjusts the precise placement of the sensor (in various dimensions) on the subject.

Apparatus for Hemodynamic Assessment

Referring now to FIG. 1, an exemplary embodiment of the hemodynamic assessment apparatus 100 of the invention is described. This embodiment generally comprises an actuator assembly 300 mated with a sensor assembly 200. The actuator 300 is optionally in the form of a wrist bracelet as shown, and controls the movement of the sensor/applanation element 210 of the sensor assembly 200. The sensor assembly 200 comprises a flexible frame 204 with a foam backing 206. The sensor assembly 200 is further described in detail with regard to FIGS. 2-2g below.

In the illustrated embodiment, this structure is preferably made disposable through use of inexpensive materials (e.g., low-cost plastic moldings) and design features facilitating such disposability; however in certain applications (such as where the apparatus is intended for reuse), more durable materials may be chosen.

Noticeably distinct from the prior art, the aforementioned embodiment of the hemodynamic assessment apparatus does not comprise an alignment apparatus (e.g., paddle) as in prior embodiments. Rather, the exemplary embodiment of the present invention is adapted to utilize automatic zeroing, a technique by which the sensor element is aligned without the use of extraneous apparatus. Thus, the sensor element will be automatically positioned in the most appropriate location relative to the subject's anatomy.

In one variant of the invention, the frame 204 incorporates arrows that are used to align with a line drawn on the patient's arm (e.g., by the caregiver after manually locating the optimal location on the subject's anatomy which represents the artery location). The clinician palpates and marks the artery with a pen on the skin, drawing a line where the artery lies. Then he/she lines the two arrows on the top of the frame with the line drawn on the skin.

Figure 2:
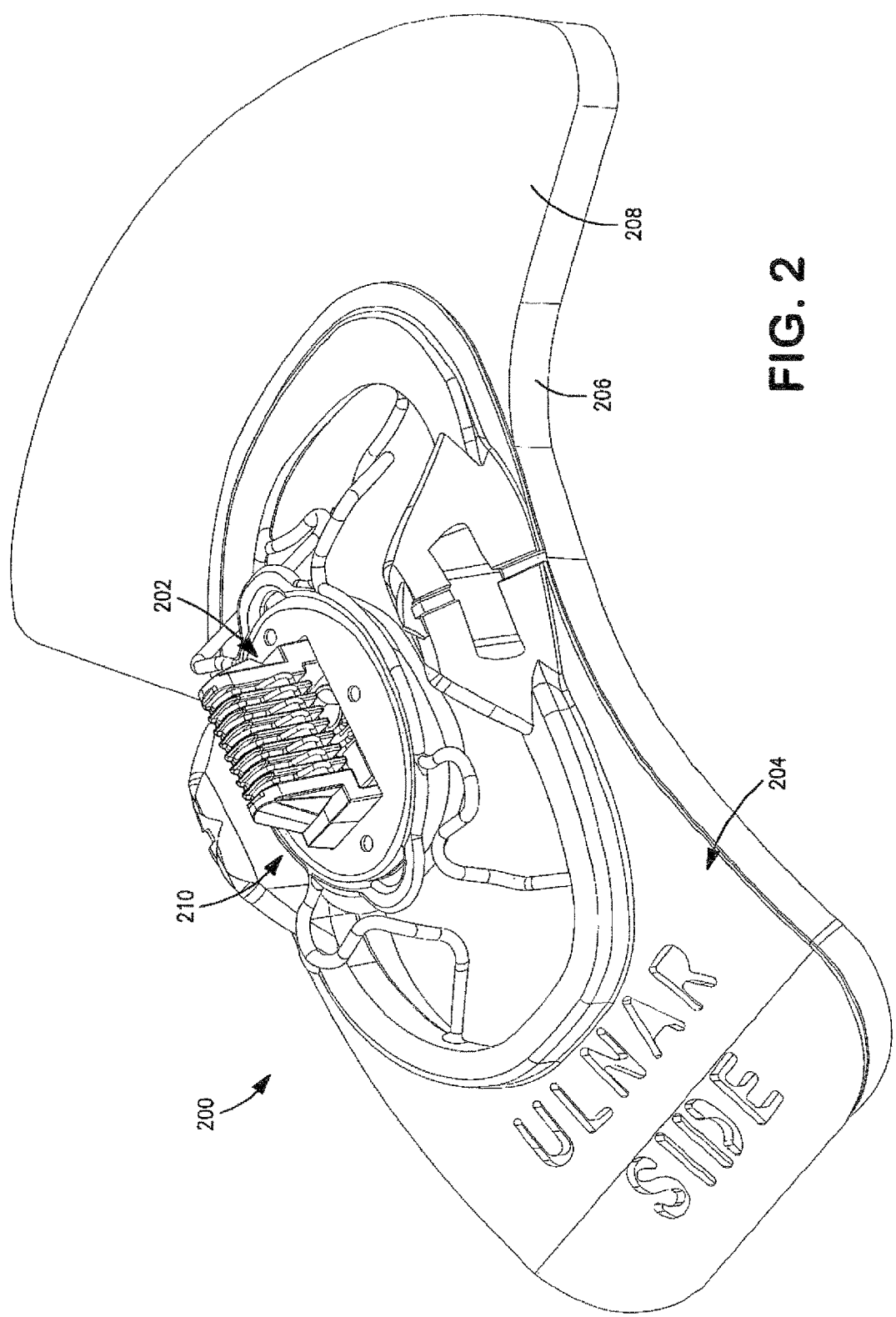
FIG. 2 is a perspective view of one exemplary embodiment of the sensor assembly used with the apparatus of FIG. 1.

FIG. 2 depicts an exemplary embodiment of a sensor assembly 200. As illustrated, the sensor assembly 200 generally comprises a sensor connector assembly 202 (described in more detail in FIG. 2a-2e below) mounted on a sensor element 210, the element 210 being movably coupled to a flexible frame element 204 (described in further detail in FIG. 2f below), the latter which comprises a foam backing 206 (described in detail in FIG. 2g below).

In one embodiment, the sensor assembly 200 further comprises a label or other covering 208 which (i) covers the end of the foam which would otherwise be bare adhesive, and (ii) shows inter alia a user the correct placement of the device on the arm. Since the frame ends at the edge of the label, the foam is much more flexible, which allows it to conform better to the wrist. The label of the illustrated allows us to use one piece of foam that has adhesive on the top surface, to attach it to the frame, although it will be appreciated that other approaches may be used with equal success.

FIG. 2a illustrates the sensor connector assembly 202 which is comprised of a sensor connector 218 disposed on the sensor/applanation element 210. The sensor connector assembly 202 is further comprised of an electrically erasable programmable read-only memory (EEPROM) IC (element 248 on FIG. 2c), one or more pressure sensor elements (e.g., a transducer, strain beam device, piezoelectric or piezoresistive device, etc.), and a multi-layered housing element 214. These components of the sensor connector assembly 202 are illustrated and described in more detail in FIGS. 2b-2e and the accompanying discussion below.

The sensor/applanation element 210 is used to compress the tissue surrounding the blood vessel of interest under the force of the actuator 300, and to thereby apply force to the blood vessel wall so as to overcome the wall or hoop stress thereof. The applanation element 210 has a specially designed configuration adapted to mitigate the effects of transfer loss in a simple, repeatable, and reliable way such that it can be either (i) ignored or (ii) compensated for as part of the tonometric measurement.

The sensor connector assembly 202 further comprises a sensor connector 218, which may be viewed in more detail in FIG. 2b.

FIG. 2b depicts the sensor connector 218. The sensor connector is comprised of a plurality of conductors (e.g. wires 220 or alternatively flat strips, conductive traces, etc.). The wires follow along the periphery of one side of a generally pyramidal or tapered spool or block 224, although other profiles and shapes (e.g., conic, trapezoidal, hemispherical, hexagonal, etc.) are contemplated. The use of a shape helps to guide the connector into the receptacle without getting stuck or misaligned. The wires 220 are maintained electrically separate from each other by a series of ridges 222 along the inner portion of the pyramidal spool 224. The wires 220 are adapted such that when the sensor connector assembly 202 is mated with the connector recess 308 the actuator 300, the wires 220 are positioned to electrically communicate with the electrical contacts 312 of the recess 308. The exemplary embodiment of the sensor connector 218 as illustrated in FIG. 2b further depicts a plurality of wire terminals 226. It is appreciated that although eight wire terminals 226 are illustrated in the exemplary embodiment, any number of such terminals may be utilized consistent with the present invention. The plurality of exposed wires 220 is made large so as to provide maximum opportunity for making a good connection with the corresponding electrical connector in the actuator, described below. In the illustrated embodiment, two of the eight wires egress from one side of the assembly, and six from the others, so as to provide mechanical stability during assembly.

The overall tapered pyramidal shape of the top portion of the sensor connector 218 is merely exemplary in that it promotes a frictional coupling between the sensor assembly 200 and the associated actuator receptacle 304. Thus, the associated actuator receptacle 304 (see FIG. 3 and associated discussion below) is effectively the inverse of the top portion of the sensor connector 218; i.e., it is adapted to generally match at least most of the contours of the sensor connector 218 and the frame lip 282 (discussed below). Indentions 212 are provided in the top surface of the bottom portion of the sensor element to allow mating to the top portion thereof. The top portion of the sensor connector 218 can be considered the "male" element, and the associated actuator receptacle 304 the "female" element. The substantially square shape of the base of the sensor connector 218 advantageously controls rotation of the sensor connector 218 with respect to the actuator receptacle 304 under torsional loads. This coupling of the two elements 218, 304 allows for a highly rigid and non-compliant joint between the actuator 300 and sensor, assembly 200 in the applanation (normal) dimension, thereby effectively eliminating errors in resulting hemodynamic measurements which could arise from such compliance. A discussion of the contribution of the frame lip 282 to this coupling is discussed below.

As illustrated in FIG. 2c, the sensor connector assembly 202 further comprises a printed circuit board 240 on which the connector 218 is disposed. The tabs 228 of the sensor connector 218 facilitate mounting the sensor connector 218 on the printed circuit board 240 as they are received in tab recesses (not shown) on the circuit board 240.

The sensor connector wire terminals 226 are situated such that when the sensor connector 218 is mounted on the printed circuit board 240, the wire terminals 226 align with the sensor connector terminal electrical contacts 244 on the printed circuit board 240. It is through this contact that information from the sensor (not shown) is transmitted, although other approaches may be used.

Also as depicted in FIG. 2c, the sensor connector assembly 202 comprises the sensing elements (not shown) accommodated within a lower sensor housing 246 below the sensor connector 218. A retention feature such as, for example, cantilever snap, is used to secure the lower housing element 246 to the other layers of the sensor connector assembly 202. In another embodiment, the sensor has four leads that protrude, and are formed into "legs" that are soldered to the other side of the board. The part is also adhered to the board to ensure it is rigidly held.

The circular feature shown is the vent port protruding from the pressure sensor (246). This vent is a cylinder that sticks through the board and thereby allows for the pressure die in the sensor to be a gage device. It has effectively a vent on each side of the pressure diaphragm, with one side communicating with the silicone rubber gel which touches the skin and the other side of the diaphragm communicating with the air in the environment in which it is being us The sensor elements (not shown) are situated within the lower sensor housing 246 such that the sensor is positioned to contact the skin of a subject. The bias element 216 then forms a substantially elliptical profile "pocket" adapted to house the sensor elements.

Also in FIG. 2c, an electrically erasable programmable read-only memory (EEPROM) IC 248 or other memory device is disposed on the printed circuit board 240. The EEPROM chip terminals 250 are situated such that when the EEPROM chip 248 is disposed on the printed circuit board 240, the terminals 250 are placed in contact with EEPROM terminal electrical contacts 252 on the circuit board 240.

The circular feature 242 shown is a vent port protruding from the pressure sensor 246. This vent is a cylinder that protrudes through the board and thereby allows for the pressure die in the sensor to be a gauge device. It comprises a vent on each side of the pressure diaphragm, with one side communicating with the silicone rubber gel which touches the skin of the subject, and the other side of the diaphragm communicating with the air in the environment in which it is being used. This allows for the device to not read the atmospheric pressure differences at different altitudes.

Given the components described above, the sensor connector assembly 202 in this embodiment is adapted to contain the necessary circuitry and sensor electronics such that the assembly 202, when mated with the actuator 300 will be able to transmit electrical signals from the sensor element(s) (e.g., pressure transducer, not shown) to the actuator 300 without the use of other apparatus. In this way, the assembly can detect and monitor pressure immediately upon electrical connection of the sensor assembly 200 to the actuator 300, and the need to form any other electrical or mechanical connections is obviated. Therefore, the above-described embodiment determines and constantly monitors hemodynamic pressure efficiently and with increased ease of operation.

FIG. 2d illustrates the disposition of the exemplary multi-layered housing element 214 around the printed circuit board 240 containing the EEPROM chip 248 and sensor connector 218. The multi-layered housing element 214, inter alia, helps maintain and encase the printed circuit board 240 and its components. Therefore, the face of the housing element 214 contains an indentation that is substantially formed to suit the printed circuit board 240. Further, the face of the housing element 214 contains a protrusion 260 which aligns with the printed circuit board indention 254 (FIG. 2c). It is of note that each layer of the multi-layered housing element 214 includes various protrusions and complimentary indentions so that the layers may fit together in a unique manner, and may be held together without adhesives or other such mechanisms if desired. Alternatively, the various features can be obviated in favor of such an adhesive or other mechanism. It is appreciated that other mechanisms for hold the housing elements together may be utilized consistent with the present invention. Further, a single layered housing element may also be substituted in place of the multi-layered configuration described herein. In one variant, the assembly is made as a "pallet" of boards that are snapped apart. The connectors and EEPROMs are soldered to one side of this array or matrix of boards, then the sensor is glued and then soldered to the other side of each board. Once separated, they form the assembly shown is FIG. 2c. The housings comprise a housing and a cap to hold the board in the housing. The exemplary cap is made out of ABS plastic and is placed over the connector and then solvent-bonded to the housing, effectively trapping the connector, the board and the sensor in place. Alternative configurations considered included ultrasonically welding the cap to the housing, or snapping the cap to the housing features to allow this.

Figure 2E:
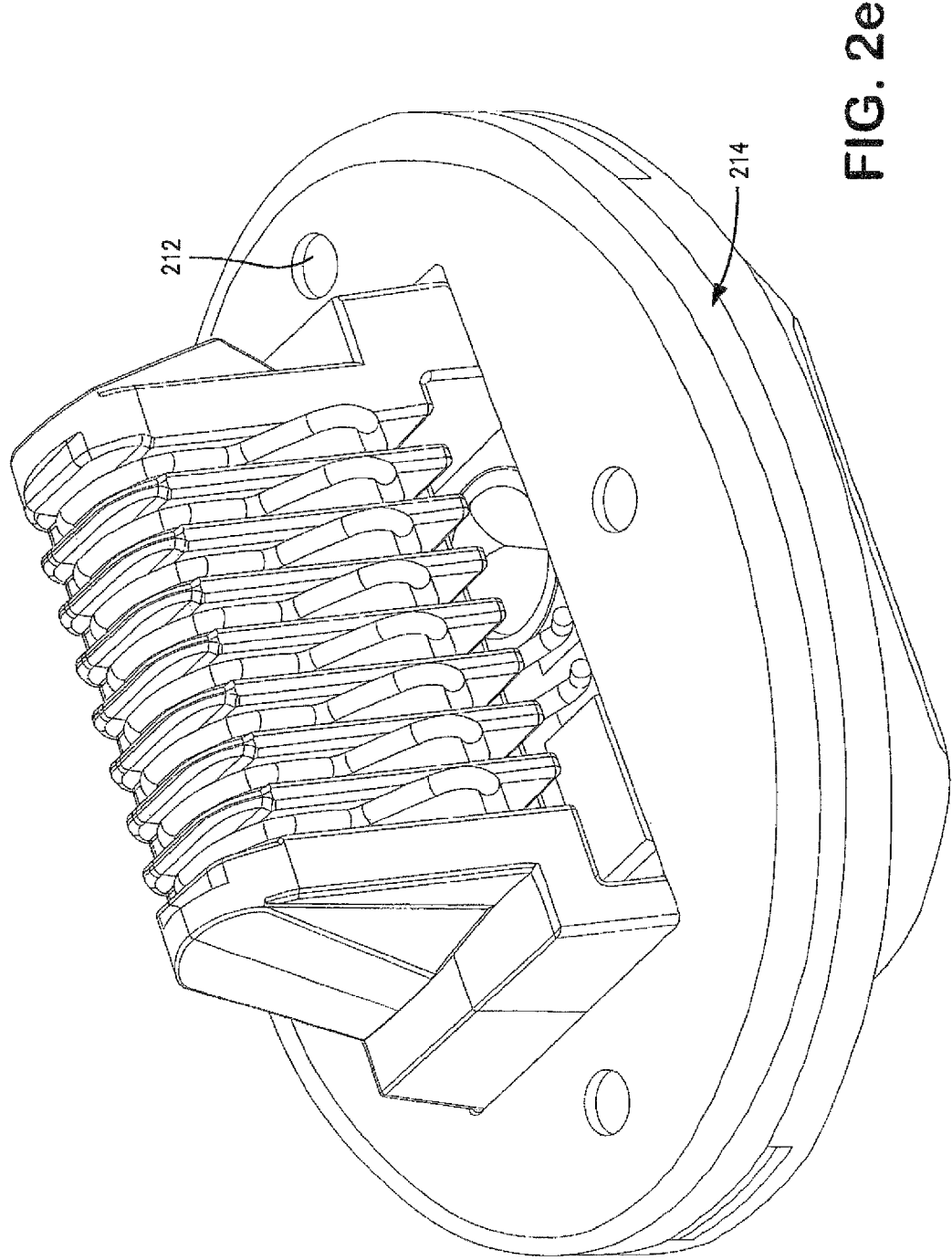
FIG. 2e is an illustration of the exemplary embodiment of the sensor connector assembly placed in the connector housing and encapsulated by the upper encapsulation.

FIG. 2e demonstrates the placement of the final layer of the example multi-layer housing element 214. This layer of the housing element 214 further includes a plurality of coupling indentions 212a, 212b, 212c which are adapted to cooperate in coupling the sensor connector assembly 202 to its parent actuator 300 (described in greater detail with respect to FIGS. 3-3d herein). It is appreciated that different configurations and number of coupling mechanisms may be utilized to facilitate mating of the sensor connector assembly 202 with the actuator 300.

Referring again to FIG. 2a, the biasing element 216 of the sensor connector assembly 202 surrounds the outer/bottom edge portions of the multi-layered housing element 214 as well as the portion of the pressure sensor element (not shown) which will come into contact with the subject's skin. The biasing element 216 is, in one embodiment, made wholly from a silicone-based encapsulation material. There are at least two distinct advantages of using encapsulation material as the biasing element 216 for smaller embodiments such as the sensor connector assembly 202 of FIGS. 2 and 2a. First, the use of encapsulation material eases fabrication, as smaller size foam is more difficult to handle in production environments. Second, the bottom edge of the biasing element 216 can now have a radius or other transitional shape molded into the profile, reducing the size of the shearing effect on the skin as the sensor connector assembly 202 is pressed into the skin during lateral and proximal movements. It will be noted also that the otherwise "unitary" encapsulation material shown may also be comprised of two or more independent or coupled component moldings if desired.

It will also be appreciated that consistent with other embodiment(s) of the sensor assembly 200, other schemes may be used with the invention, such as not using the sensor connector assembly 202 as the applanation element. For example, an actuator coupled to an applanation element (not shown) separate or otherwise decoupled from the pressure or other sensor(s) may be employed. While significant economies and advantages relate to the exemplary use of the sensor as the applanation element, this is by no means a requirement for practicing the invention. Hence, the present invention should in no way be considered limited to embodiments wherein the sensor (i.e. the sensor connector assembly 202) also acts as the applanation mechanism.

While the biasing element 216 in the present embodiment comprises a silicone rubber based compound that is applied over the active face of the pressure transducer (and selective portions of the housing element 214) to provide coupling between the active face and the subject's skin, other materials which provide sufficient pressure coupling, whether alone or in conjunction with an external coupling medium (such as a gel or liquid of the type well known in the art) may be used as well. Further, in some embodiments, it may be desirable to construct the biasing element from, or coat it with, materials having low coefficients of friction such as e.g. Teflon™, etc.

Moreover, the bias element need not necessarily be uniform in material construction, but rather could be constructed using hybrid materials integrated to perform the desirable functions of the bias element when used in combination. This may include mixing materials, doping the silicone material to provide other desirable properties, coating the material (as previously described), and so forth. Myriad other design choices would be readily apparent to those of ordinary skill given the present disclosure.

In the exemplary embodiment, the bias element 216 is formed by molding the encapsulant (e.g., silicone compound) around the sensor element (not shown) and housing element 214 after the sensor (not shown) has been placed in the housing 214. This ensures that the encapsulant completely covers the sensor, and fills all voids. In effect, the bias element 216 is molded around the sensor (not shown), thereby ensuring a conformal fit and direct coupling between the encapsulant material and the sensor's active face. It will also be recognized that the sensor and applanation element configuration of FIG. 2a is merely exemplary, and other sensor configurations (e.g., single or multiple transducer, homogeneous or heterogeneous sensors (i.e., combined with the same or other types of sensors), and/or using different bias element geometry) may be used consistent with the present invention.

Figure 2F:
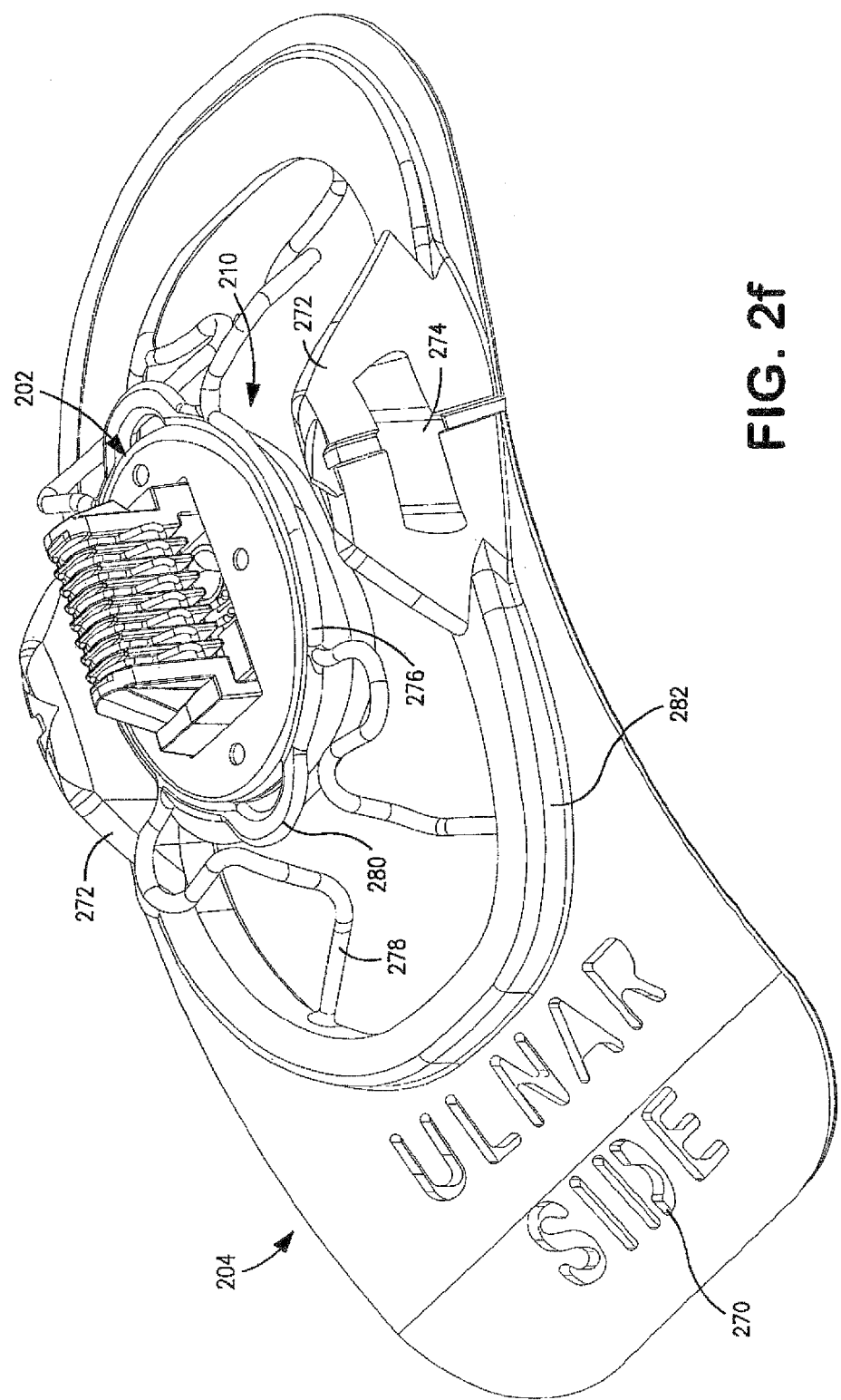
FIG. 2f is an illustration of one exemplary embodiment of the sensor connector assembly mounted in the flexible frame.

FIG. 2f depicts the sensor/applanation element 210 and its connector assembly 202 mounted movably within the flexible frame element 204. This exemplary embodiment generally comprises a single frame element 204, which is distinguished over prior art implementations having two frame elements. This approach advantageously simplifies the construction of the apparatus, and also provides opportunities for reducing manufacturing cost while also increasing ease of use by the caregiver or subject being monitored.

The single frame element 204 comprises a generally planar (yet curved), thin profile. This approach (i.e., flatter and thinner material) has significant advantages over the prior art including allowing for increased conformity and adaptation to the anatomy of the subject being monitored. The single frame element 204 is advantageously shaped from a polymer molding formed from polypropylene or polyethylene, although other materials and degrees of flexibility may be used consistent with the principles of the present invention.

The Assignee hereof has also found through experimentation that placing the sensor at a more distal location with respect to the wrist and forearm can result in more consistent system performance and better accuracy. Thus, in the embodiment shown in FIG. 2f the frame 204 of the apparatus is notably smaller in surface area with respect to the portion of the frame 204 that extends on the radial side of the apparatus when it is disposed on a human subject. Utilizing a shape with a minimized frame in this area permits the apparatus to be placed at a more distal location while avoiding the thenar eminence (the body of muscle on the palm of the human hand just beneath the thumb). It is noted however that the aforementioned level of flexibility of the frame 204 is further selected to permit some deformation and accommodation by the frame to the shape and radius of the wrist of the subject as well. Accordingly, the foregoing optional features coordinate to provide a more comfortable and well-fitted frame and sensing apparatus, thereby also increasing accuracy of the measurements obtained thereby.

Also illustrated in FIG. 2f, the exemplary embodiment of the frame 204 presents the user with a miniature placement "map" by way of the graphic illustration of the location of local physiology through labeling and the like. For example, at one end of the frame element 204, the lettering "ulnar side" 270 is produced by way of cutout on the frame element 204, although other approaches such as labels, painting/marking, etc. may be used to accomplish this function. This phrase refers the user to the fact that this ulnar side of the frame element should be positioned on the ulnar side of the patient's forearm. The cut-through design of the illustrated embodiment is advantageous in that the lettering can be more legible to a user of a device than other approaches, and cannot be removed or fall off. After proper placement, the user then deforms the frame 204 around the subject's wrist, thereby adhering the frame 204 in place on the patient's forearm using an adhesive placed on the contact (skin) side of the frame and exposed after its protective sheet is removed.

Also depicted in FIG. 2f, a set of ribs or risers 272 are provided; these ribs 272 are notable as they are received within corresponding features (e.g., cavities) present on the actuator 300. The embodiment of FIG. 2f advantageously simplifies the design and molding of the alignment apparatus frame 204, as compared to prior art embodiments which utilize complex structures that fit both within and outside of actuator cavities. The ribs 272 are further adapted to comprise an intrusion or aperture 274 on the outer surface of each with respect to the sensor connector assembly 202. The intrusions 274 are adapted to receive complementary tabs 322 associated with the actuator 300 thereby allowing the actuator 300 to be set in place (i.e. mated with the sensor assembly 200) and unable to significantly rotate. Note that in the illustrated embodiment, there is 10° rotation built in to allow for the shape variation in the forearms of different subjects. Once the device is rotated beyond that limit the sides of the cavities press against the sides of the snap features on the actuator and that forces the frame to deflect which releases the frame from the actuator. To install the actuator onto the frame one must simply press the actuator down onto the frame at which point the whole frame acts as a snap fit and latches to the actuator.

This feature ensures an easily formed, robust, and uninterrupted connection of the actuator 300 to the sensor assembly 200.

As demonstrated in FIG. 2f, coupling of the sensor connector assembly 202 to the frame element 204 in the exemplary embodiment is accomplished using a flexible and resilient serpentine-like suspension loop 276 and associated suspending arms 278.

The suspension loop 276 is attached to the circumference of the multi-layered housing element 214; the loop substantially encircles the sensor connector assembly 202 and fits within a groove formed in the outer edge of the sensor element 210, although other arrangements may be used. As illustrated in the figure, sections of the suspension loop 276 are formed so as not to be in contact with the housing element 214 as previously described. These sections form arches 280 which receive the pins 314 located within the actuator receptacle 304 when the actuator 300 is mated with the sensor assembly 200. However, other methods for assisting and maintaining the sensor connector assembly 202 within the actuator receptacle 304 may be used with equal success.

Note that in the illustrated embodiment, the end loops also facilitate putting the elliptical ring feature of the suspension loop around the groove of the sensor multi-layer assembly. They allow the ring to "stretch" for assembly.

The suspending arms 278 are coupled rigidly to the frame element 204 via integral injection molding, adhesive or other means and attached flexibly to the suspension loop 276. The suspending arms 278 in the present embodiment provide sufficient "slack" such that the frame element 204 and the sensor element 210 can move to an appreciable degree laterally (and in other degrees of freedom) within the frame 204, thereby allowing the actuator 300 to move the sensor element 210 relative to the radial artery during execution of its positioning algorithm and automatic zeroing of the sensor. The present invention also allows for such freedom of movement in the proximal direction as well as in the direction of applanation or blood vessel compression. Moreover, sufficient slack may be provided in the suspending arms 278 to allow a desired degree of proximal movement of the sensor element 210 by the actuator 300, as well as rotation of the sensor element in the X-Y plane (i.e., "yaw" of the sensor assembly about its vertical axis). Other arrangements may also be used, such alternatives being readily implemented by those of ordinary skill in the mechanical arts.

It will be further noted that in the illustrated embodiment, the suspension loop 276 and associated suspending arms 278 maintain the sensor element 210 (including most notably the active surface of the assembly) in a raised position completely disengaged or elevated above the surface of the skin. This advantageously allows the operator and the system to verify no bias of the sensor and pressure transducer during periods when bias is undesirable, such as during calibration of the sensor.

The exemplary zeroing algorithm includes various features, including (i) checking for a quiescent state wherein the output from the sensor is steady (e.g., monotonic, although not necessarily constant, due to e.g., sensor warmup or other temperature effects), which does not happen when the sensor is touching skin, and/or (ii) retracting the sensor up into the actuator and "dithering" the applanation position in order to ensure that if the pressure does not change the sensor is truly off the skin. Either or both of these approaches may be used.

FIG. 2f also depicts an exemplary frame lip 282 which is formed along the circumference of the central aperture of the frame element 204. The frame lip 282 is designed to fit snugly within the actuator receptacle 304 thereby holding the sensor assembly 200 in contact with the actuator 300. The lip also adds rigidity to the frame in the direction in which the snap fits act for the attachment of the frame to the actuator. It also prohibits the actuator from being placed on backwards by interfering with features on the opposite side of the actuator.

Thus the actuator receptacle 304, as discussed below, is comprised of a "moat" to accept the protruding frame lip 282. The frame lip 282 configuration of the exemplary embodiment is preferable to other prior art configurations because, inter alia, this configuration permits a single-step, unobstructed connection of the sensor assembly 200 to the actuator 300. There is also better automatic guidance, thereby minimizing the chance of a mismatch.

Figure 2G:
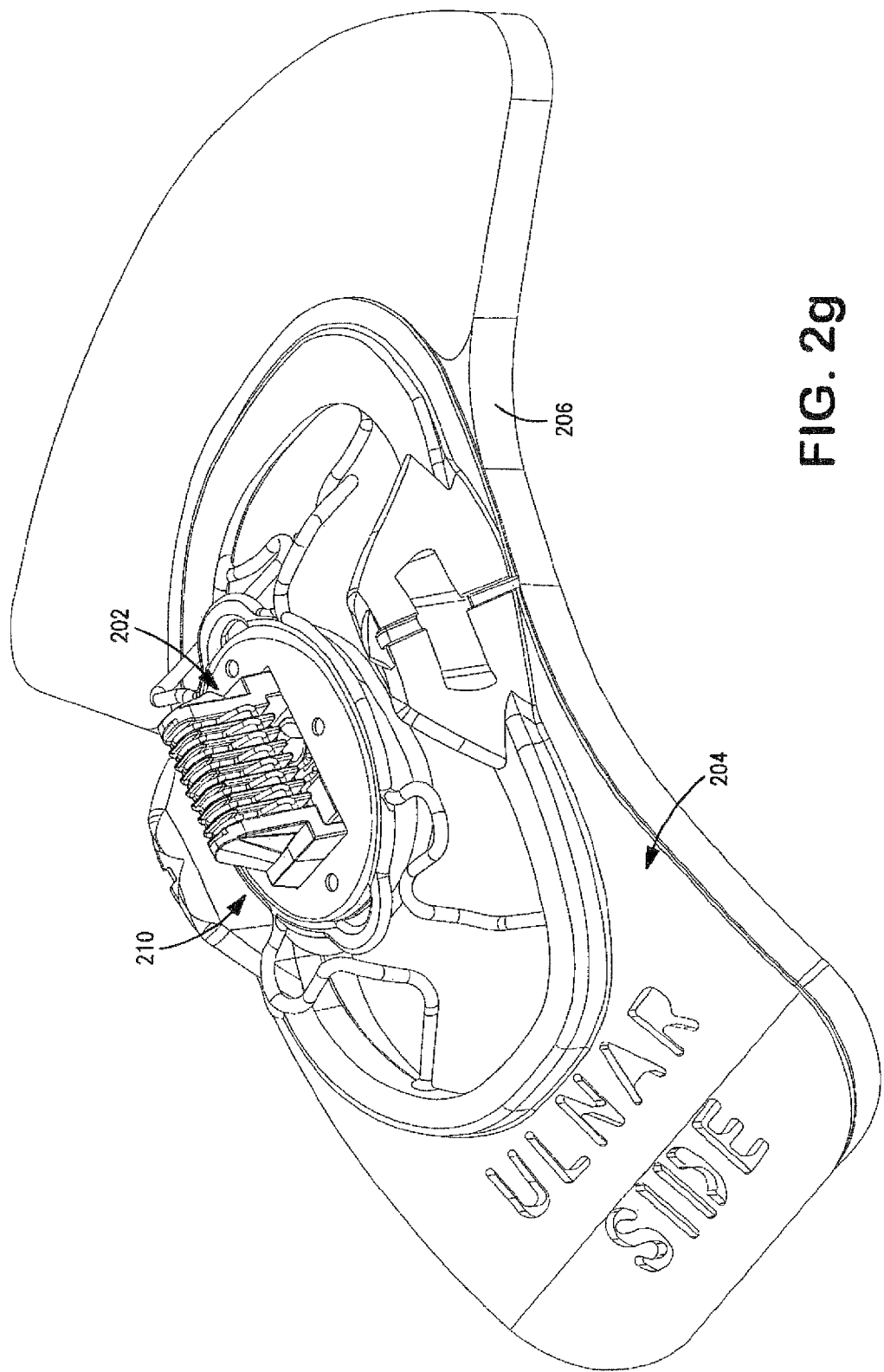
FIG. 2g is an illustration of one exemplary embodiment of the sensor connector assembly and frame mounted on a foam backing.

Referring now to FIG. 2g, the foam backing 206 onto which the frame element 204 is disposed is described in detail. The foam backing 206 is comprised of compliant foam with adhesive surfaces that is mounted to the contact-side of the element 204. The foam backing can advantageously be conformed to the unique profiles and shapes associated with living subjects of varying shapes and sizes.

As described above, the frame element 204 is substantially minimized with respect to the radial portion in this embodiment as compared to prior art embodiments. Accordingly, the foam backing 206 may be adapted to extend the radial portion of the sensor assembly 200 in order to permit increased surface area for attachment to a subject. As discussed above, the shape of the foam backing 206 will be such that the thenar eminence ("thumb muscle") of a human subject continues to be accommodated. Thus, the attachment of the sensor assembly 200 is not obstructed, but rather conforms to the natural raises and indentations in a subject's anatomy.

The adhesive on the underside of the compliant foam backing 206 is adapted such that when the frame element 204 is disposed atop the subject's skin, it bonds to the skin, the frame element 204 deforming somewhat to match the surface contour of the skin. The adhesive is selected so as to provide a firm and long-lasting bond (especially under potentially moist conditions resulting from patient perspiration, etc.), yet be readily removed when disposal is desired without significant discomfort to the subject. However, other means for maintaining the frame element 204 in a constant position with respect to the subject's anatomy may be used, including for example Velcro straps, tape, application of an adhesive directly to the underside of the frame element 204 itself, etc. In another embodiment, a thermally- or light-sensitive frame material is used that allows the initially deformable and pliable frame element to become substantially more rigid upon exposure to heat, light, or other such "curing" process.

A low-cost removable backing sheet (e.g., waxed or coated on one side) of the type well known in the adhesive arts may be used to cover the aforementioned adhesive (not shown) disposed on the interior or contact side of the frame element 204 prior to use, so as to preclude compromise thereof. The user simply peels off the backing sheet, places the frame element 204 on the desired anatomy location, and gently compresses it against the subject's skin to form the aforementioned bond, deforming the frame element 204 as needed to the contour of the subject's anatomy. The adhesive bond is strong enough, and the frame element pliable enough, such that any deformation of the frame element is substantially preserved by the bond as discussed above.

As discussed above, a notable difference between the foregoing exemplary embodiment of the sensor assembly 200 described above and that of the prior art is the absence of a "paddle" element in the present invention. The paddle element is used in the prior art to place the sensor assembly in a desired location relative to the subject's anatomy. In the present invention, however, the necessity for the user to place the sensor assembly manually is obviated in favor of an automatic zeroing process. In this embodiment, the automatic zeroing advantageously simplifies the operation of the apparatus, and also provides opportunities for reducing manufacturing cost, because there is no need to manufacture a paddle, assemble it, and so forth. Rather than aligning the artery or other blood vessel between the two parallel lines of the paddle (e.g., by aligning the longitudinal axis of the target portion of the artery between the two parallel features of the reticle), the present invention permits a user to merely place the apparatus on the subjects anatomy, and line up the arrow marks on the sides of the frame with the line of the artery. Further, the straight edges of the frame are supposed to line up with the "wrist break" where the wrist ends and the hand starts. The shape of the foam is also supposed to seat the frame in close proximity to where it is needed due to the flare shape which simulates the thump flaring to one side. Thus, the present invention greatly increases the ease of use by the caregiver or subject being monitored.

In the illustrated embodiment, the substantially elliptical sensor shape also accommodates moving the edge of the frame 204 closer to the centerline of the apparatus, so that the frame 204 can accommodate the thenar eminence. The reduced sensor size and profile in the lateral/medial direction (as compared to other embodiment described herein) also allows the frame to be smaller than it otherwise would, and the sides of the sensor impinge less on tendons that run in the proximal/distal direction.

Moreover, by making the sensor smaller in all directions, the surface area being pressed into the skin is reduced, which reduces the power needed to drive the sensor into the skin. By reducing the power required, the applanation/positioning mechanisms can be made smaller, and less electrical power is required (important for "stand-alone" or battery powered variants).

Another advantage of the smaller elliptically-shaped sensor element 210 is that because of the reduced lateral/medial length, the sensor impinges less on tendons during sensor travel (e.g., in the lateral/medial direction) as previously noted, thereby allowing the sensor to slide across the surface of the skin in a more uniform and smooth manner.

This provides enhanced performance during, inter alia, lateral search phase monitoring. In addition, the elliptical shape of the sensor 210 of FIGS. 2-2g provides a continuously curved surface on the outer periphery of the sensor connector assembly 202, facilitating movements in both the lateral and proximal axes by reducing shear effects. Specifically, in one aspect, the elimination of "corners" on the elliptical variant makes changes in direction and movement smoother in all directions, and when coupled with the curved sidewall or cross-sectional profile of the assembly, allows for some degree of roll, pitch, and/or yaw of the sensor relative to the tissue surface (or conversely, greater irregularities within the tissue shape or surface) without adversely impacting movement of the sensor assembly across the tissue.

In yet another embodiment, hemodynamic parameter measurements are obtained using an apparatus comprising a multi-use or reusable sensor element (see FIG. 2i; discussed below), and a limited (e.g., one-time) use disposable frame element (see FIG. 2h; discussed below). Costs associated with manufacturing the sensor element are generally significantly higher than those associated with the frame and its components. Hence, using this configuration, the operation of the device is more cost effective in that the operator can merely purchase a new single-use frame element for each subject or patient, and reuse (to a desired extent) a single sensor, even across multiple patients. The reuse of the sensor is enabled in large part through the provision of a diaphragm or membrane which protects or insulates the sensor from any direct contact with the subject's skin.

The overall functions and structure of the frame and sensor are generally similar in many regards to those described above, with certain distinctions described in greater detail subsequently herein.

Figure 2H:
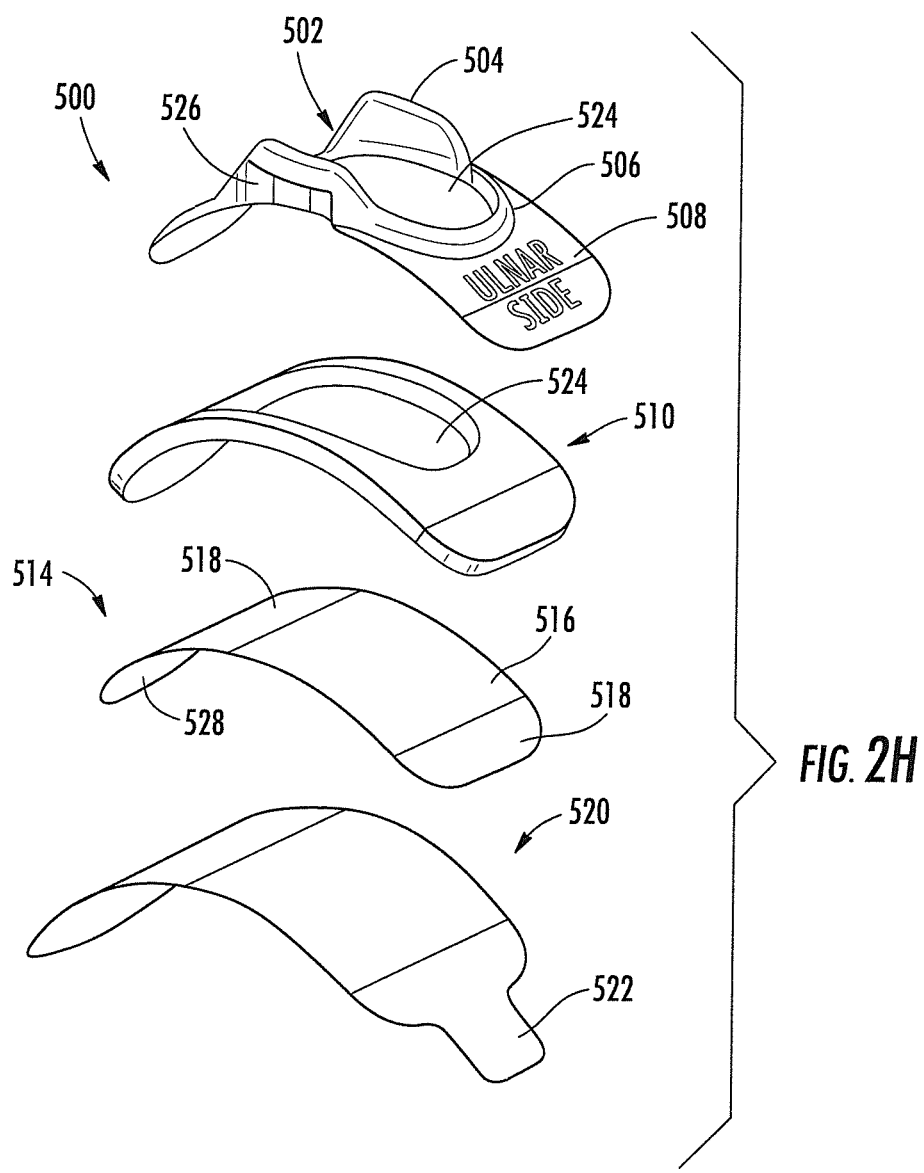
FIG. 2h is a perspective exploded view of the disposable frame and associated components according to another embodiment of the invention.
Figure 21:
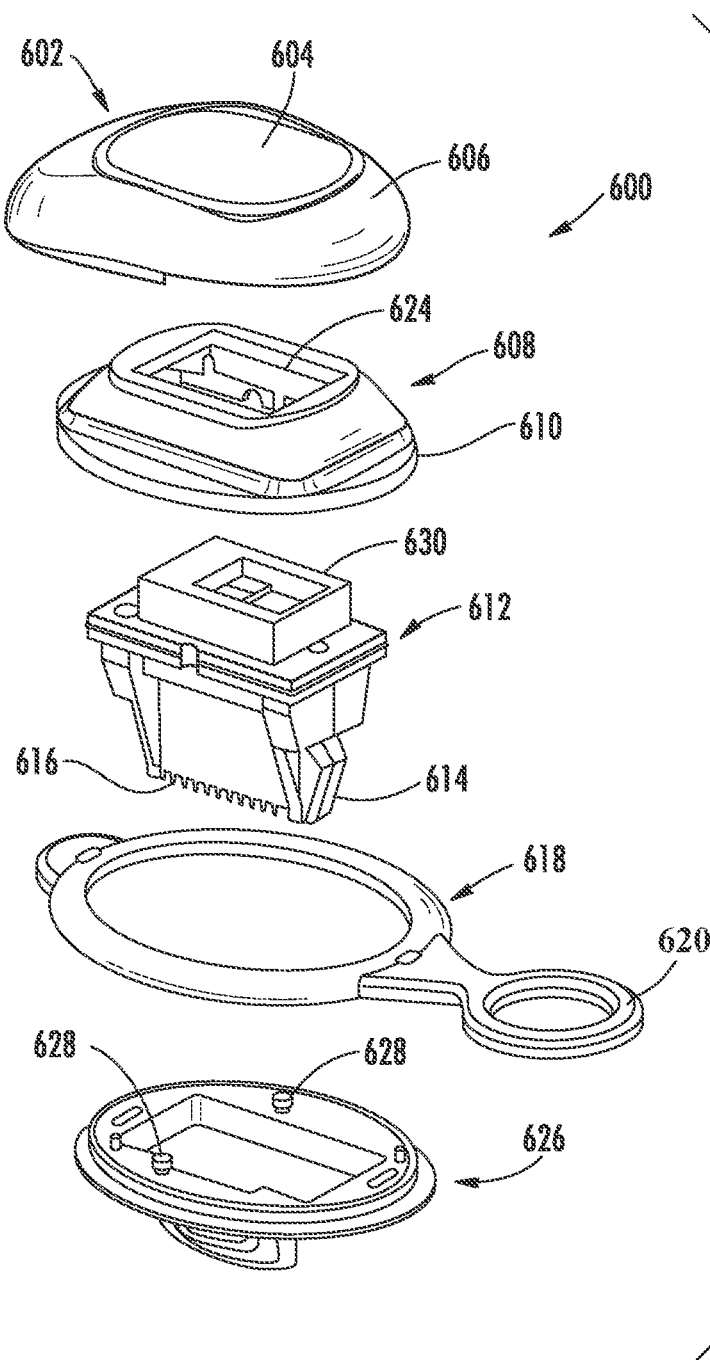

Referring now to FIG. 2h, an exemplary embodiment of a disposable frame 500 is illustrated. As shown, the disposable frame 500 comprises a frame component 502, a frame liner 510, a diaphragm or membrane 514, and a membrane liner 520.

The sensor frame component 502 is comprised of a somewhat compliant or flexible and resilient polymer molding formed from polyethylene, although other materials and degrees of flexibility may be used. As discussed above, the particular curved shape of the frame is designed to accommodate the medial portion of the wrist of most humans, while the aforementioned level of flexibility permits deformation of the overall shape of the frame element 500 to the particular shape and radius of the wrist of a given subject. Alternatively, different sizes and shapes of frame elements 500 may be provided for different placements and/or different subject dimensions. Still further, the frame may be configured to be asymmetric having one end larger than the other, so as to e.g., facilitate easier grasping during application or removal, better fit on the subject, space for labeling or diagrams, etc.

The frame element 502 may also comprise one or more accommodations for various portions of a user's anatomy, such as the well known styloid process of the wrist area. These accommodations not only make the frame element fit better onto the subject, but also advantageously help with coarse alignment of the frame (and hence sensor). For instance, in one variant, the frame element 502 comprises a distortion or notch formed in the radial side so to accommodate the styloid process. It will also be recognized, however, that the use of a somewhat flexible and resilient frame material also advantageously allows the frame 502 to distort somewhat in order to better adapt to the physiology of each individual subject. In this regard, a "one size fits all" approach to the frame 502 may be used, which simplifies manufacturing, inventory, etc. It will be appreciated, however, that custom-fit frame elements (e.g., one size for larger individuals, one size for children, etc.) may be readily used consistent with the present invention.

Moreover, the styloid process is aligned with the reticle during application, as described in greater detail subsequently herein with respect to FIG. 5.

The sensor frame 502 of FIG. 2h comprises an aperture 524 for receiving one or more sensor elements (discussed below). The aperture 524 of the exemplary frame is sized to accommodate a single sensor, as well as a significant amount of movement thereof (e.g., in the lateral and proximal dimensions) within the aperture. This advantageously allows for a less precise placement of the frame 502 on the subject's anatomy, since the host device (e.g., actuator) has more freedom to reposition the sensor laterally and proximally to achieve optimal coupling of the sensor to the blood vessel.

The sensor frame component 502 comprises one or more features 504, 506 for securing a host device (e.g., actuator 300) thereto. In the illustrated embodiment, a set of ribs or risers 504 are molded into the frame 502, which are received within corresponding features (e.g., cavities) present on the actuator 300. The risers 504 are shaped to have indentations or apertures 526 on an exterior surface thereof. The actuator 300 is coupled (via the dowels 322 on its skirt periphery; see discussion of actuator 300 elsewhere herein) to the indentations 526 of the sensor frame component 502 of the disposable frame 500. The coupling of the frame 500 and actuator 300 (via the indentations 526) also provides positive relative positioning and anti-rotation of the actuator and the sensor element (discussed below).

Although such coupling significantly impedes rotation of the actuator and/or the frame, it is noted that a small degree of rotation may be designed-in to allow for, e.g., the shape variation in the forearms of different subjects. Rotation beyond this prescribed amount causes the frame to release from the actuator. As with the embodiments discussed above, the actuator is installed onto the frame by pressing the actuator (via the host device; e.g., bracelet) down onto the frame, allowing for a snap fit.

The frame 500 of FIG. 2h also comprises a lip 506 formed along the circumference of the aperture 524. The frame lip 506 fits within a corresponding feature of the actuator 300 (such as the actuator receptacle 304) thereby holding the frame assembly 500 in contact with the actuator 300. The lip 506 is configured in one exemplary embodiment to prevent the actuator from being placed on the frame incorrectly (for example, backwards), such through well known means such as keying, asymmetry of shape, etc.

The sensor frame 502 may additionally comprise words 508 or other visual indicia which help the operator or subject rapidly position the assembly over the forearm in the proper orientation. In the illustrated embodiment, an "ulnar side" is distinguished. Additionally or alternatively, a "radial side" may be given. The words 508 may be printed on the surface of the frame 502, cut-out from or molded into the body of the frame 502, placed as a sticker on top of the frame 502, etc. It will also be appreciated that other verbiage, placements, indicators, graphics or features may be used consistent with the invention to aid in user operation and placement of the various components, such as arrows, color coding, pictures/drawings, particular textures, Braille characters, etc.

In a further embodiment, the sensor frame 502 may comprise outwardly extending portions (not shown) configured to clip onto the sides of an actuator 300 or host device, thereby providing further support for coupling of the frame 500 to the actuator/host.

The frame liner 510 of the illustrated embodiment of FIG. 2h is attached to the underside of the sensor frame component 502 (i.e., the side thereof which is shaped to conform to the surface of the skin of the subject). The frame liner 510 is made of substantially flexible polymer; e.g., polyethylene foam, although other materials and levels of flexibility up to and including inflexible materials may be used if desired. The frame liner 510 is used in the present embodiment to pad or cushion the frame element 500 as it is placed atop the surface of the subject's skin, although it will be appreciated that such liner is in no way required for practicing the invention. The frame liner 510 is shaped to accommodate the general shape of the sensor frame 502 and the aforementioned aperture 524.

In an alternate embodiment, the frame liner comprises one or more layers of material sprayed or otherwise coated onto the bottom of the frame 502, or is impregnated into the frame material (i.e., is not a discrete component itself).

The diaphragm or membrane 514 portion of the frame element 500 in the illustrated embodiment adheres to the underside of the frame component 502. The membrane optionally comprises one or more placement portion(s) 518. The placement portions 518 ensure the membrane is coupled to the frame liner 510 at points surrounding the aperture 524. The transparent portion 516 of the membrane 514 traverses or covers the underside of the aperture 524 (i.e., the side which will come into contact with the surface of the skin of the subject), and provides a protective barrier and transfer medium between the surface of the subject's skin and the sensor element when the latter is received within the aperture 524 of the frame 502. The transparent portion 516 may be comprised of a substantially transparent thin material, such as e.g., a clear polyester polymer or polyethylene) and is placed across the aperture 524 substantially taut so as to not impede movement of sensor across the surface thereof. Tautness of the transparent portion 516 is provided by placement of the placement portion 518 of the membrane along the underside of the foam liner 510. The thickness and physical properties of the membrane 514 are in one implementation chosen to have specific durometer (hardness) and thickness parameters. For example, the durometer may be between 10-55 Shore A, the tensile strength may be between 2.0-8.0 lbs/inch, and the thickness may range from 0.001-0.010 inches. However, it will be appreciated that other values may be substituted based on the particular physiologic parameter(s) being assessed, type of application, and/or type of sensor used.

The membrane 514 may also be coated on one side (at least in the aperture region) with a lubricant, such as one solid, liquid, or powdered in nature, that facilitates lateral/proximal movement of the sensor relative to the upper (lubricated) surface of the membrane. As previously noted, the exemplary oval or elliptical shape of the sensor element (and its substantially "rounded" corners) further facilitate such movement without binding or "jerkiness" that might otherwise occur.

The diaphragm or membrane 514 further includes an adhesive 528 on its underside such that when the frame 500 is disposed atop the subject's skin, it (via the adhesive on the membrane) bonds to the skin, the frame element 500 being capable of deforming somewhat if required to match the surface contour of the skin. The adhesive is advantageously selected so as to provide a firm and moisture (e.g., sweat) resistant bond, yet be readily removed when disposal is desired without significant discomfort to the subject. Other means for maintaining the frame element 500 in a constant position with respect to the subject's anatomy may be used as well, including for example Velcro straps, tape, etc., whether alone or in conjunction with the foregoing.

A low-cost removable backing sheet or liner 520 (e.g., waxed or coated on one side) of the type well known in the adhesive arts is used in the illustrated embodiment in order to cover the adhesive 528 prior to use, so to preclude compromise thereof. During use, the user simply peels off the backing sheet 520 via a tab located thereon 522, places the frame element 500 at the desired location on the surface of the subject's skin, and gently compresses it against the subject's skin to form the aforementioned bond, deforming the frame element as needed to the contour of the subject's anatomy (which also facilitates more surface area contact for the adhesive with the skin).

The membrane 514 of the illustrated embodiment further includes an alignment mechanism or device (not shown), which aids the user/operator in properly positioning the frame element 500 at the onset. In one embodiment, this alignment device comprises a reticle or symbol disposed upon (e.g., printed or rendered on) the substantially transparent portion 516 of the membrane 514 itself. The reticle may take any number of shapes, such as "cross-hairs", two or more parallel lines, a dot, a series of concentric rings ("target"), etc. Once the desired specific monitoring location has been identified (such as by the user/operator finding a suitable pulse point on the surface of the subject's medial region using their finger or other technique, and marking this location with a marker or the like), the backing sheet 520 is peeled off, and the reticle of the membrane 514 aligned over the marked pulse point by viewing the reticle through the aperture 524. The user/operator then simply presses the adhesive surface 528 against the subject's skin to affix the frame 500 in place. As previously noted, the placement of the frame 500 advantageously need not be very precise (thereby allowing the system to be more robust and insensitive to operator errors or variations in use), since (i) the host device (actuator) of the exemplary embodiment includes a vessel location algorithm/routine, and (ii) the frame 502 includes a sufficiently sized aperture to permit the sensor to move laterally and proximally so as to correct for such imprecision of placement.

Alternatively, the reticle may be disposed or formed in other places, such as for example as part of the frame element 502 itself (e.g., molded as part thereof, with frangible links to permit removal after placement), or as a sticker or removable layer overlying the top portion of the frame element 502. In yet another embodiment, a removable or moveable paddle of the type previously referenced herein may be attached to the frame element 500 and used for alignment, then moved or removed when the frame is attached to the actuator and sensor.

Referring now to FIG. 2i, a reusable sensor element 600 according to one embodiment of the invention is illustrated. The sensor element 600, as in the embodiments discussed above, may in addition to sensing also be used as an applanation element to compress the tissue surrounding the blood vessel of interest under the force of the actuator 300, and to thereby apply force to the blood vessel wall so as to overcome the wall or hoop stress thereof. In one variant, the applanation element 600 is specifically designed to mitigate the effects of transfer loss as discussed above. In yet another embodiment the sensor 600 is not used as the applanation element, instead a separate applanation element (in one variant decoupled from the pressure or other sensor(s)) may be employed.

As shown, the sensor element 600 generally comprises a sensor connector element 612, a lower sensor housing 608, and an upper housing element 626, a portion of the sensor element 600 is encapsulated in a silicone encapsulant layer 602 of the type previously described herein. Note that as used herein, the terms "upper" and "lower" are purely relative; i.e., in the embodiment illustrated in FIG. 2i, the sensor element 600 is shown inverted from its normal orientation, although this is in no way limiting on the invention. In yet another embodiment, one or more surfaces of the sensor element 600 (for example an active surface thereof) may be unencapsulated.

The overall profile of the sensor 600 in the illustrated embodiment is an elliptical or oval shape (such as those described above with respect to FIGS. 2-2g). The dimensions of the sensor 600 are selected so as to allow for greater lateral/proximal travel of the sensor 600 within the aperture 524 of the frame 500 without a need to reposition the frame. Likewise, the overall size and shape of the frame 600 may be made smaller or otherwise adjusted as needed. Various additional advantages of the overall elliptical shape of the sensor 600 are discussed above, and equally applicable to the reusable sensor 600 discussed with respect to FIG. 2i.

The silicone encapsulant layer 602 comprises a silicone-based encapsulant 606 which encircles at least the lower housing 608 portion of the sensor element 600 and, in one embodiment, forms the biasing element thereof. Various advantages of using encapsulation material as the biasing element are discussed above with respect to FIGS. 2-2g, and are likewise applicable to the reusable sensor 600 discussed herein.

The encapsulation layer 602 further comprises a portion 604 covering the active surface of the sensor (e.g., pressure transducer). The encapsulation material disposed at the active surface may be of the same silicone-based material used to encircle the entire sensor. Alternatively, a thinner layer may cover this surface, or no material may be used at all. The active surface material 604, inter alia, protects the active face of the sensor from direct exposure. In the present embodiment, the active surface 604 of the encapsulant will interact directly with the membrane layer 514 of the frame element 500 so as to transfer signals (e.g., pressure variations) through the membrane and the encapsulant to the transducer active surface.

The lower housing 608 of the exemplary sensor element 600 is in the illustrated embodiment a plastic casing for the sensor connector 612. The lower housing generally comprises at least one aperture 624 which receives the lower portion of the connector element 612 (and exposes the active face of the sensor transducer), and enables the active face to protrude through the housing to the active surface 604 of the encapsulant layer 602.

The lower housing 608 further comprises a removal apparatus retainer 610, which works in conjunction with a similar feature on the upper housing 626 to retain the removal apparatus 618 in place between the upper and lower housings. The features of the upper and lower housings are held together via a series of notches 628 on the upper housing 626 which are received within one or more accommodating features (not shown) located on the platform 610. In one variant, the removal apparatus comprises a flexible (e.g., polymer or rubber) ring having a tab by which it may be grasped by a user. The sensor 600 is removed from the actuator as a unit by pulling on the removal ring 620 of the removal apparatus 618 in a direction away from the actuator/host device.

As illustrated in FIG. 2i, the sensor connector element 612 generally comprises the sensor electronics and terminals 616 disposed in a substantially pyramidal configuration. Additionally, coupling structures 614 are disposed on the surface of the sensor connector 612 to enable the sensor connector 612 to be received securely (such as by friction fit) within a receptacle of the actuator 300. The overall shape of the sensor connector as being generally pyramidal offers various advantages as discussed above with respect to the embodiments of FIGS. 2-2g.

The sensor connector element 612 is further comprised of a plurality of conductors 616 (e.g. wires or alternatively flat strips, conductive traces, etc.) which follow along the periphery of one side of a generally pyramidal housing. The conductors 616 electrically communicate with the electrical contacts 312 of the actuator 300. Although not shown, it is appreciated that the connector element 612 may be mounted on a printed circuit board, such that the conductors 616 align with electrical contacts thereon. The exemplary connector element 612 of FIG. 2i generally comprises the features discussed above with respect to FIGS. 2b-2c for mechanical stability and enhanced electrical communication.

As discussed above, the connector element 612 of the sensor 600 is comprised of an electrically erasable programmable read-only memory (EEPROM) IC (similar to element 248 of FIG. 2c above). The electrically erasable programmable read-only memory (EEPROM) IC or other circuit device or component(s) may be disposed on the printed circuit board as well.

The sensor connector element 612 may further comprise one or more sensing elements such as e.g., a pressure transducer (not shown). The sensor element(s) is/are situated such that when the sensor assembly 600 is positioned to contact the membrane of the frame element 500 (on the skin of a subject), hemodynamic parameter measurements may be made through the membrane and encapsulant.

The receptacle of the actuator (such as the second element 304 attached to the actuator 300) has a substantially complementary shape to that of the sensor connector element 612. Once secured within the actuator, the connection is highly rigid so that the sensor 600 may not substantially move with respect to the actuator.

In one embodiment, the sensor is programmed to have a finite lifetime (e.g., number of uses) or number of days. The life cycle or number of uses is specifically determined by decrementing a stored lifetime value based on minutes of use. For example, the lifetime may be 10800 minutes of use stored in the EEPROM memory as a number of minutes remaining. This value is decremented by the host device during use. This approach allows the sensor to be used multiple times, but not exceed its design lifetime (which may result in degradation of performance or the components themselves). In one variant, the sensor is programmed to permit completion of an ongoing use or measurement if the boundary is crossed (e.g., 10800 minutes or 180 hours of use, from time of first use decrementing only while the host device is measuring blood pressure) is exceeded during an actual use. This advantageously permits the caregiver to complete the measurement for that subject, but no more. Once the lifetime is exceeded, the sensor is permanently disabled in that the host device will not allow a case to begin on a sensor with a value of 0 minutes remaining in its EEPROM.

The host device of the present invention is also programmed in one embodiment to allow re-entry of scaling or calibration data, such as for example body mass index (BMI) as described in co-owned U.S. Pat. No. 6,730,038 to Gallant, et al. issued May 4, 2004 and entitled "Method and apparatus for non-invasively measuring hemodynamic parameters using parametrics", incorporated herein by reference in its entirety. This capability allows, inter alia, the use of the same sensor on multiple different individual shaving different physiologic parameters (e.g., heights, weights, wrist circumferences, etc.).

Figure 3:
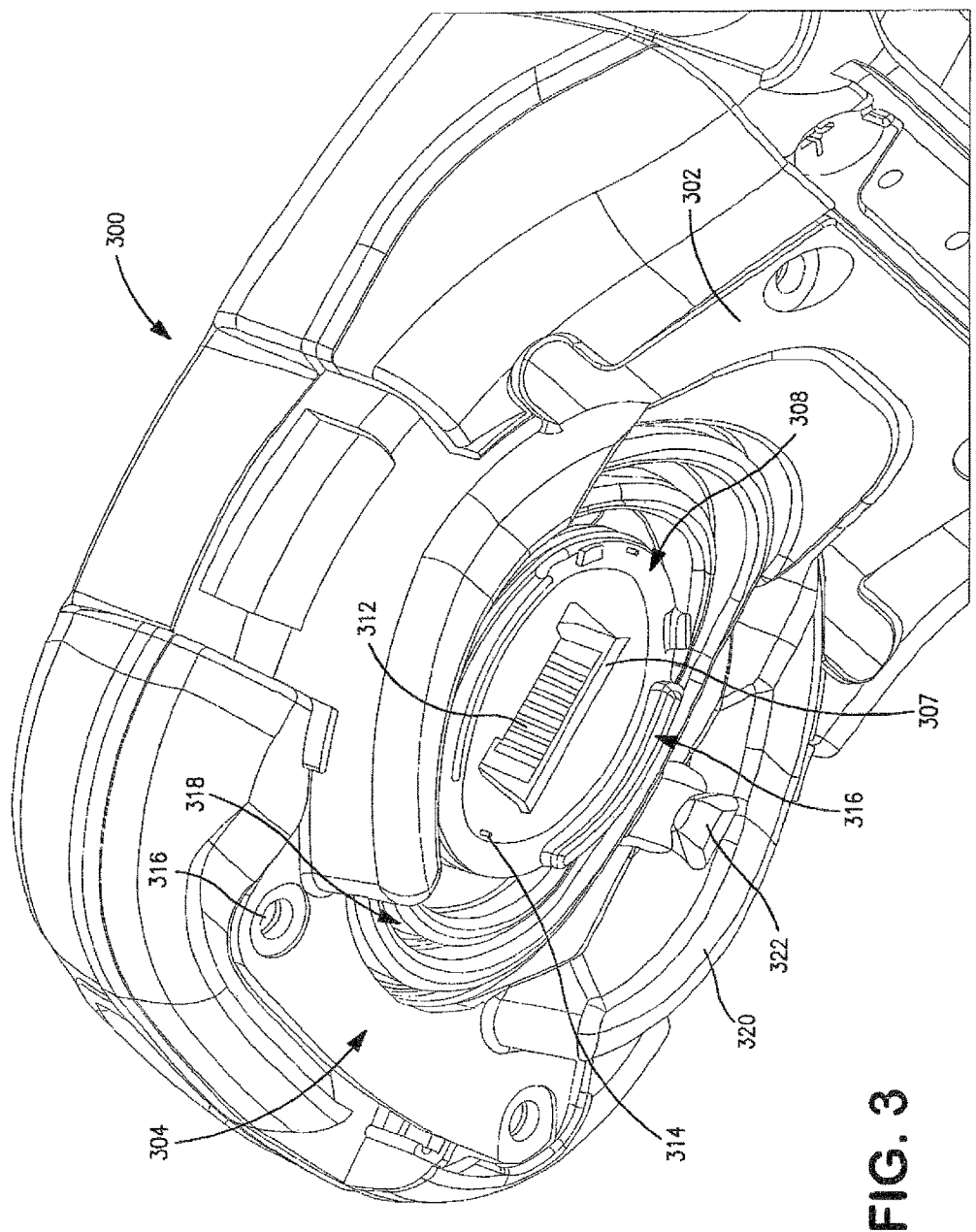
FIG. 3 is a perspective view of the underside of one exemplary embodiment of the actuator element illustrating the connector and sensor attachment plate.

Referring now to FIGS. 3-3d, one exemplary embodiment of the actuator assembly 300 of the invention is described. The actuator 300 described herein is designed to provide adjustment or movement of the position of the sensor element 210 in both sagittal and lateral (transverse) directions; however, it will be appreciated that it may be modified to provide more or less degrees of freedom (including, for example, proximal adjustment). Hence, the following embodiments are merely exemplary in nature.

FIG. 3 illustrates the underside of one embodiment of the actuator assembly 300. The underside of the actuator in this embodiment is generally comprised of an attachment plate 302 onto which various coupling mechanisms and receiving apparatus are disposed. The receiving apparatus (e.g. the actuator receptacle 304, the connector disk 310 and connector recess 308) provide cavities within which portions of the sensor connector assembly 202 are accepted when the sensor element 210 (and assembly 200) and the actuator 300 are mated. The coupling mechanisms (e.g. the frame lip receiving walls 320 and complementary tabs 322, and the actuator receptacle rings provide a secure connection between the actuator 300 and the sensor connector assembly 202. A rubber bellows 318 is also provided that allows the receptacle to move with respect to the rest of the actuator and seals the opening around the receptacle from fluid or dirt ingress. Each of these features will be discussed in detail below. It will be recognized, however, that other coupling arrangements for the secure mating of the actuator 300 to the sensor element 210 and assembly 200, whether utilizing the coupling mechanisms and receiving apparatus or not, may be employed consistent with the invention.

The exemplary attachment plate 302 further comprises a plurality of plate attachment features 306 by which the attachment plate is fastened to the underside of the actuator 300. In the exemplary embodiment of FIG. 3, the plate attachment features consist of threaded cavities which are designed permit assembly via screwing the attachment plate into the actuator 300 body. It is appreciated that other methods and techniques may be utilized to secure the attachment plate 302 to the actuator 300 body, such as, for example, via a glue, latch, or similar technique.

In the exemplary embodiment, the underside of the actuator 300 features an actuator receptacle 304. The actuator receptacle 304 is a recess in the actuator plate 302 which is adapted to receive the sensor assembly 200. The actuator receptacle 304 is comprised of a plurality of inner rings, a connector disk 310 and frame lip receiving walls 320.

The connector disk 310 is adapted to accept portions of the sensor connector assembly 202 and promote secure mating therewith. Accordingly, the connector disk 310 comprises a partial bearing ring 316 which conforms substantially to the corresponding features of the sensor connector assembly 202 and helps secure the actuator 300 in place, especially under conditions of transverse loading or rotation of the actuator 300 around the lateral or proximal axis. The connector disk 310 also comprises a plurality of pins 314 which fit into the arches 280 of the suspension loop 276. As described previously, when the actuator 300 is mated with the sensor assembly 200, the pins 314 will be received snugly within the aperture created by the suspension loop arches 280.

The connector recess 306 is disposed on the connector disk 310 of the actuator receptacle 304. The connector recess 306 is specifically adapted to accept the pyramidal sensor connector 218. Thus, it consists of an inverted pyramidal shaped recess. The inverted pyramidal shaped recess of the connector recess 306 is further adapted to maintain electrical contact with the plurality of wires 220 on the sensor connector 218 when the two 306, 218 are mated. This electrical communication occurs via placement of electrical contacts 308 on the connector recess 306 by which electrical signals are transmitted. The receptacle also has a "U" shape that precludes the connector from being put in backwards.

FIG. 3 further illustrates the frame lip receiving walls 320, which are disposed on the actuator receptacle 304. The frame lip receiving walls 320 conform substantially to the corresponding features of the frame element 204 and help secure the actuator 300 in place. Specifically, the frame lip receiving walls 320 create a moat wherein the ribs or risers 272 of the frame element 204 are fitted when the actuator 300 and sensor assembly 200 are mated. The frame lip receiving walls 320 are further adapted to include complementary tabs 322 which are designed to snap into the matching intrusions 274 on the ribs 272, thereby allowing the actuator 300 to be set in place (i.e. mated with the sensor assembly 200) and unable to rotate. When viewed from the side the receiving walls also have a shape that precludes the actuator from being put on backwards.

FIGS. 1 and 3a-3c illustrate the exemplary coupling between the actuator 300 and sensor assembly 200. As best illustrated in FIG. 1, the various coupling mechanisms (described above) are configured so as to mate the actuator 300 and sensor assembly 200 together in a unitary (but readily separable) assembly.

Figure 3A:
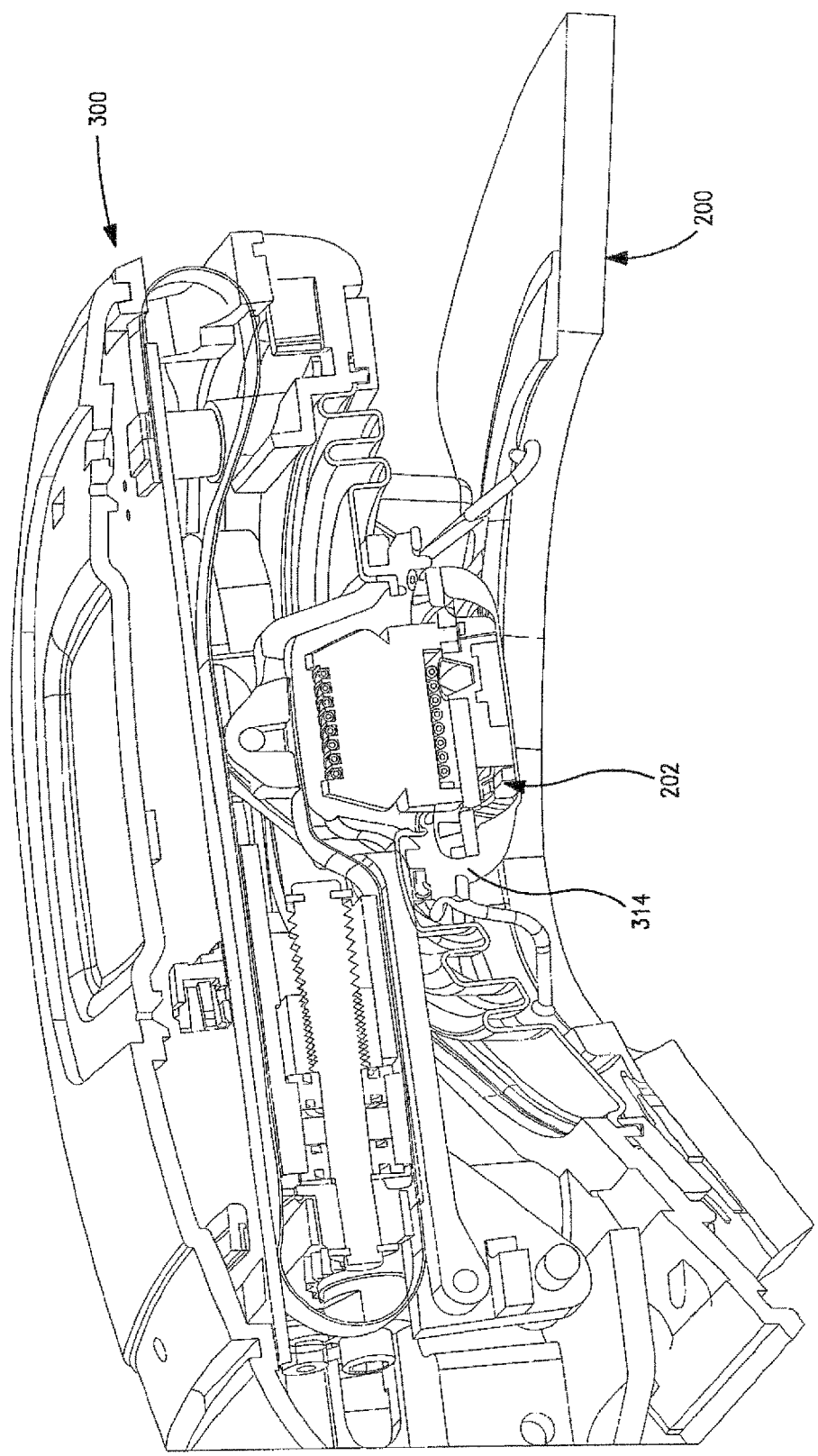
Figure 3B:
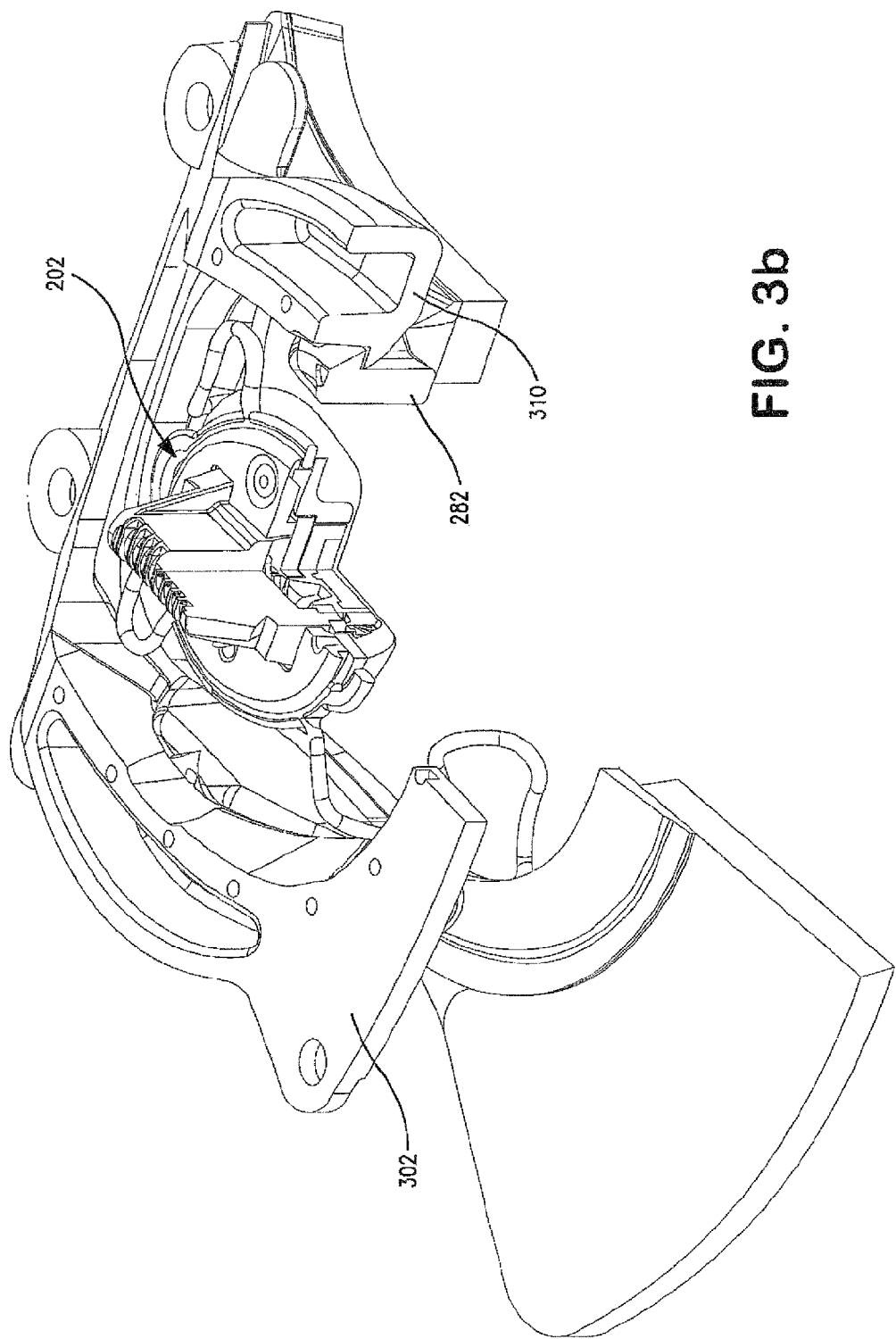
Figure 3C:
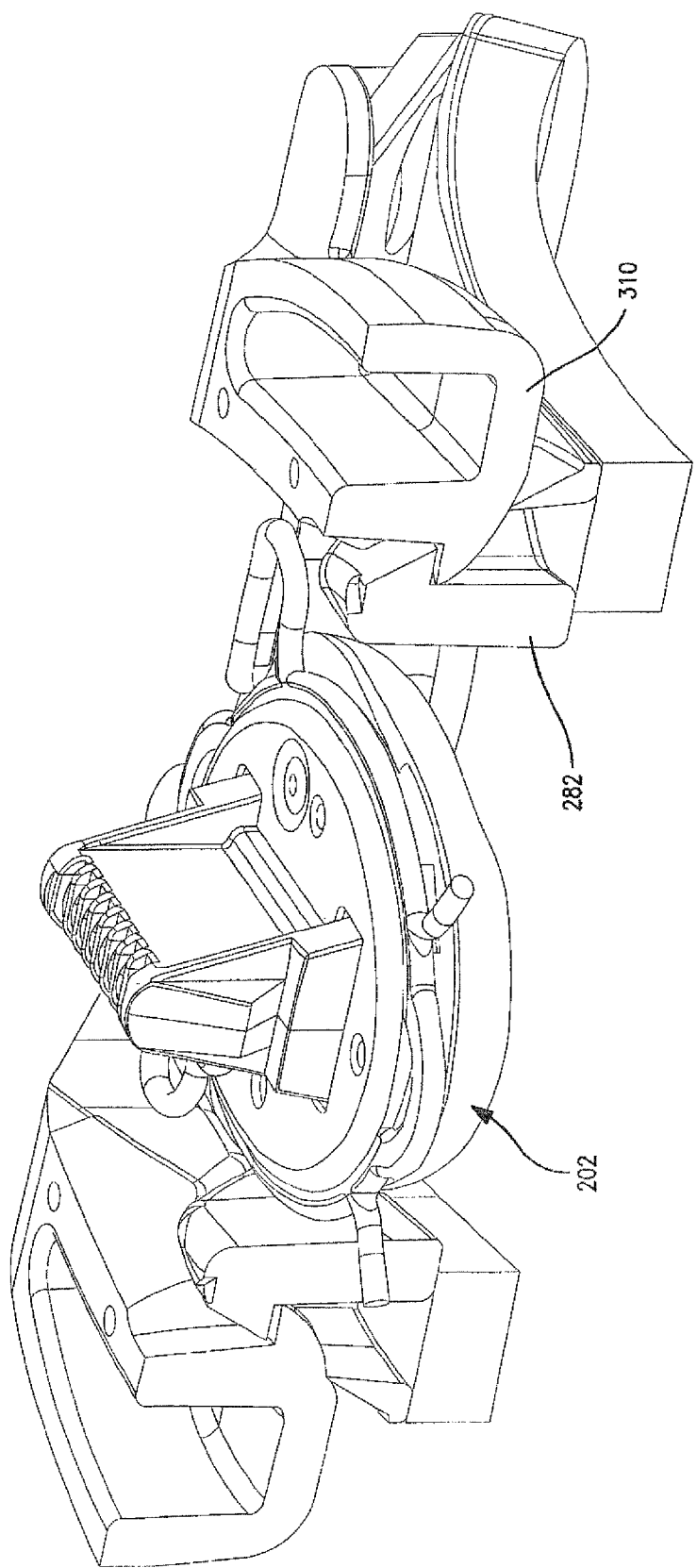
FIG. 3c is a cut-away view of the exemplary embodiment of the sensor assembly mated with the attachment plate of the actuator.

Referring to FIGS. 3a-3c, in the illustrated embodiment, the top of the sensor connector assembly 202 is substantially elongated pyramidal in shape due to the pyramidal shaped sensor connector 218. Similarly, the connector recess 308 attached to the actuator 300 is effectively the inverse of the sensor connector assembly 202 in shape; i.e., it is adapted to generally match the contours of the sensor connector assembly 202 and the alignment and retention features almost exactly. Hence, portions of the sensor connector assembly 202 which are received into the actuator 300 can be considered the "male" element, while the connector recess 308 is considered the "female" element. The substantially square shape of the base of the sensor connector 218 aids in controlling rotation of the connector recess 308 with respect to the sensor assembly 200 under torsional load. This coupling of the two elements 218, 308 allows for a highly rigid and non-compliant joint between the actuator and sensor assembly in the applanation (normal dimension), thereby effectively eliminating errors in resulting hemodynamic measurements which would arise from such compliance. This design, however, also includes enough tolerance between the coupling components to facilitate easy decoupling of the sensor assembly 200 from the actuator 30. The serpentine like suspending arms 278 provide more than sufficient strength to prevent separation of the sensor connector assembly 202 from its parent sensor assembly 200 while still permitting movement therein; the sensor assembly 200 is specifically configured such that, under all attitudes, the sensor connector assembly 202 will separate from its coupling to the actuator 300 well before the serpentine arms 278 yield significantly.

It will be noted that the elongated pyramid shape of the coupling elements further allows for coupling of the two devices under conditions of substantial misalignment; i.e., where the apex of the sensor connector assembly 202 is displaced somewhat in the lateral (i.e., X-Y) plane from the corresponding connector recess 308 of the actuator 300, and/or the sensor assembly 200 is rotated or cocked with respect to the actuator 300 prior to coupling. This feature aids in ease of clinical operation, in that the instrument can tolerate some misalignment of the sensor and actuator (the latter due to, e.g., the actuator arm of the actuator 300 (not shown) not being in perfect alignment over the sensor assembly 200 and sensor element 210).

It will further be recognized that while the illustrated embodiment comprises elongated substantially pyramid-shaped elements, other shapes and sizes may be utilized with success. For example, the apparatus may comprise complementary conic or frustoconical sections. As yet another alternative, a substantially spherical shape could be utilized. Other alternatives include use of multiple "domes" and/or alignment features, inversion of the first and second elements (i.e., the first element being substantially female and the second element being male), or even devices utilizing electronic sensors to aid in alignment of the two elements.

In one embodiment of the hemodynamic assessment apparatus 100 of the invention, the apparatus is adapted to notify the user/operator of the presence of the sensor assembly (as well as the status of its coupling to the actuator 300 and the sufficiency of electrical tests of the sensor assembly) through an integrated indication. Any type of indication scheme well known to those of ordinary skill in the electronic arts may be used, including for example one or more single color LED which blinks at varying periods (including no blinking) to indicate the presence or status of the components, such as by using varying blink patters, sequences, and periods as error codes which the operator can use to diagnose problems, multiple LEDs, light pipes. Optionally, the device further comprises a circuit which evaluates parameters in the pressure transducer and thereby can determine if the connection has been made to the transducer and EEPROM. The device may also be configured to look for the information in the EEPROM to know if it is connected if desired.

FIG. 3a is a cross sectional view of the actuator 300 coupled to the sensor assembly 200. Specifically, the illustration demonstrates the electrical and mechanical connector of the sensor connector assembly 202 within the connector recess 308.

The break-away view depicted in FIG. 3b further demonstrates the precise cooperation between the sensor connector assembly 202 and the attachment plate 302. The interaction of the frame lip 282 (of the frame element 204 of the sensor assembly 200) and the frame lip receiving walls 320 is shown. However, a more detailed depiction of this interaction is available in FIG. 3c.

FIG. 3c, as discussed above, is an illustration of the latching mechanism of the frame lip 282 and receiving walls 320. As shown best in FIG. 3, the underside of the actuator 300 is also configured to include two ridges or walls 320 with complementary tabs 322. As shown in FIG. 2f, the sensor assembly 200 is configured to include risers or ribs 272 with corresponding intrusions 274. The tabs 322 of the actuator 300 fit within the intrusions 274 of the sensor assembly 200 as shown. The snaps on the attachment plate do indeed snap into the recesses in the sides of the frame ribs (element 322 fits into element 274), As shown best in FIG. 3, the underside of the actuator 300 is configured to include two ridges or walls 320. As shown in FIG. 2f, the sensor assembly 200 is configured to include a frame lip 282. The frame lip does not interlock with anything in the actuator; rather it sits below the actuator. The frame lip also make the frame stiffer in that area which improves the snap of the latching tabs on the underside of the actuator to the frame.

The interior components (not shown) of the actuator 300 will be of the type described in Assignee's co-pending U.S. patent application Ser. No. 10/961,460 entitled "Compact Apparatus and Methods For Non-Invasively Measuring Hemodynamic Parameters" filed Oct. 7, 2004 which Assignee hereby incorporates by reference in its entirety. These generally comprise, inter alia, a motor chassis assembly with associated sensor drive coupling, and substrate (e.g., PCB) assembly.

It will further be recognized that an exemplary embodiment of the actuator mechanism would allow for the separation of the movement of the sensor connector assembly in the various directions; i.e., applanation, lateral, and proximal. Specifically, the actuator mechanism would permit concurrent yet independent movement in the various directions, as well as allow for a highly compact and space/weight efficient actuator. An exemplary actuator mechanism would further be adapted so as to minimize the number of components within the actuator (including the motors), thereby reducing electrical power consumption as well as any effect on pressure measurements resulting from the translation of a mass within the actuator during such measurements.

Methodology

Figure 4:
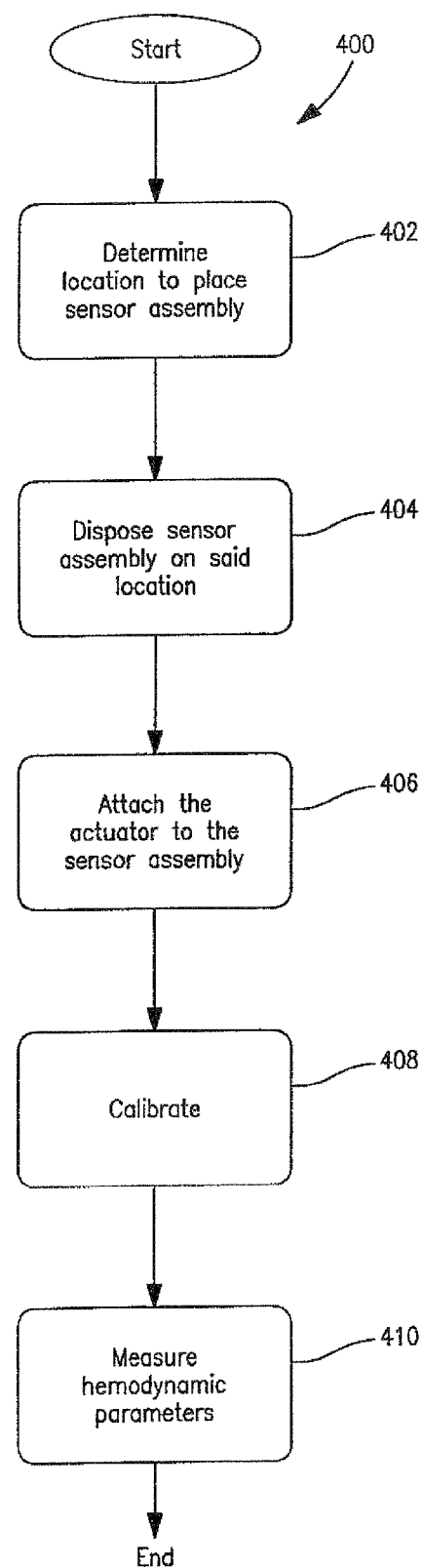
FIG. 4 is a logical flow diagram of one embodiment of the method by which the hemodynamic assessment apparatus of the invention may be utilized.

Referring now to FIG. 4, the general method 400 of positioning a sensor with respect to the anatomy of the subject and recurrently measuring the blood pressure of the subject is now described. It will be recognized that while the following discussion is cast in terms of the placement of a tonometric pressure sensor (e.g., silicon strain beam device) used for measuring arterial blood pressure, the methodology is equally applicable to both other types of sensors and other parts of the subject's anatomy, human or otherwise.

As shown in FIG. 4, the illustrated embodiment of the method 400 generally comprises first determining the location of the anatomy on which the apparatus is to be placed (step 402).

Next, the sensor is disposed relative to the marker (step 404). Specifically, in this step of the method, the user or clinician removes the backing sheet to expose the adhesive on the foam backing 206, and then bonds the frame element 204 to the subject's skin, such that the sensor connector assembly 202 is aligned generally over the pulse point of interest. The sensor is automatically zeroed (e.g., by the zeroing algorithm previously described) once placed on the subject's anatomy, and may also be adjusted laterally and or proximally according to a placement or locating algorithm of the type referenced elsewhere herein, thereby obviating a need for manual precise placement. In the exemplary embodiment, the frame element 204 and sensor connector assembly 202 come "assembled" and pre-packaged, such that the user merely opens the package, removes the sensor assembly 200 (including installed sensor connector assembly 202), and removes the backing sheet from the adhesive and places the frame element 204 as previously described.

As per step 406, the actuator 300 is securely mated with the sensor assembly. In an alternative embodiment, an optional wrist brace is first attached to the subject so as to provide stability to the subject's anatomy. The actuator 300 is then attached to the sensor assembly 200 and wrist brace. As described above, in one embodiment, an indicator will signify when the actuator 300 is properly mated with the sensor assembly 200.

In step 408, the device is "zeroed" and calibrated if required.

Lastly, in step 410, the blood pressure or other parameter(s) of the subject are measured using the sensor(s) subsequent to the calibration (step 408).

Specifically, the sensor position is maintained with respect to the anatomy between measurements using the frame element 204 and adhesive on foam backing 206 as well as the optional wrist brace. These cooperate to maintain the sensor element 210 generally atop the desired pulse point of the subject even after the actuator 300 is decoupled from the sensor. Herein lies a significant advantage of the present invention, in that the actuator 300 (and even the remainder of the hemodynamic monitoring apparatus 100, including brace) can be removed from the subject, leaving the sensor assembly 200 and hence sensor element 210 in place. It may be desirable to remove actuator 300 for example where transport of the subject is desired and the present location has dedicated equipment which must remain, or the monitored subject must have the apparatus 100 removed to permit another procedure (such as post-surgical cleaning, rotation of the subject's body, etc.). The sensor element 210 is maintained effectively constant with respect to the subject pulse point because it is securely attached to the frame element 204 via the suspension loop 276.

Hence, when it is again desired to monitor the subject using the sensor, the bracelet with actuator 300 (or another similar device at the destination), if used, is fitted to the subject. The user/caregiver then merely places the bracelet and presses to attach the actuator 300 to the sensor element 210 (and sensor assembly 200) since the sensor assembly is still disposed in the same location with the frame element 204 as when the first actuator was decoupled. The sensor is automatically zeroed, as described above, accordingly, no use of any alignment apparatus or other techniques for positioning the sensor "from scratch" is needed, thereby saving time and cost. This feature further allows for more clinically significant or comparable results since the same sensor is used with effectively identical placement on the same subject; hence, and differences noted between the first and second measurements discussed above are likely not an artifact of the measurement apparatus 100.

It will be further recognized that while two measurements are described above, the sensor assembly 200 and methodology of the invention allow for multiple such sequential decoupling-movement-recoupling events without having any significant effect on the accuracy of any measurements.

While the foregoing method has been found by the Assignee hereof to have substantial benefits including ease of use and low cost, it will be recognized that any number of different combinations of these or similar steps may be used (as well as different apparatus). For example, it is feasible that the manufacturer may wish to provide the components as a kit, which the user assembles.

As yet even a further alternative, a "marker" may be used in conjunction with the frame. For example, the marker may comprise a tangible marker or sight (e.g., plastic reticle), light source (such as an LED, incandescent bulb, or even low-energy laser light) which is projected onto the desired pulse point of the subject. This latter approach has the advantage that no physical removal of the marker is required; rather, the sensor assembly 200 can simply be put into place over the pulse point, thereby interrupting the light beam with no physical interference or deleterious effects.

Alternatively, an acoustic or ultrasonic marker (or marker based on a physical parameter sensed from the subject such as pressure) can be employed. The sensor or array may be used to precisely localize the pulse point using for example a search algorithm, such as that described in Assignee's co-pending applications previously incorporated herein, to find the optimal lateral position. This advantageously obviates the need for a reticle or other marker, since the onus is on the clinician/user to place the frame 204 properly within at least the proximal dimension. Such search method can also be extended into the proximal dimension if desired, such by including an actuator with a proximal drive motor, and a broader frame dimension.

Clearly, myriad other different combinations and configurations of the basic methodology of (i) positioning a marker with respect to a point; (ii) disposing a sensor with respect to the marker, and (iii) disposing the sensor proximate the desired point, will be recognized by those of ordinary skill given the present disclosure. The present discussion should therefore in no way be considered limiting of this broader method.

As previously noted, one of the significant advantages of the present invention relates to its flexibility; i.e., that it is essentially agnostic to the hardware/firmware/software on which it is used, and can be readily adapted to various different platforms or systems for measuring hemodynamic or other physiologic parameters. For example, the methods and apparatus of the present invention are substantially compatible with, inter alia, those described in: co-pending U.S. patent application Ser. No. 10/393,660 "Method and Apparatus for Control of Non-Invasive Parameter Measurements" filed Mar. 20, 2003; co-pending U.S. patent application Ser. No. 10/269,801 entitled "Apparatus and Methods for Non-Invasively Measuring Hemodynamic Parameters" filed Oct. 11, 2002; co-pending U.S. patent application Ser. No. 10/920,990 entitled "Apparatus and Methods for Non-Invasively Measuring Hemodynamic Parameters" filed Aug. 18, 2004; co-pending patent application Ser. No. 11/336,222 entitled "Apparatus and Methods for Non-Invasively Measuring Hemodynamic Parameters" filed Jan. 20, 2006; co-pending U.S. Pat. No. 6,554,774 entitled "Method and Apparatus for Assessing Hemodynamic Parameters within the Circulatory System of a Living Subject" issued Apr. 29, 2003, each of the foregoing assigned to the Assignee hereof and incorporated by reference herein in its entirety.

Figure 5:
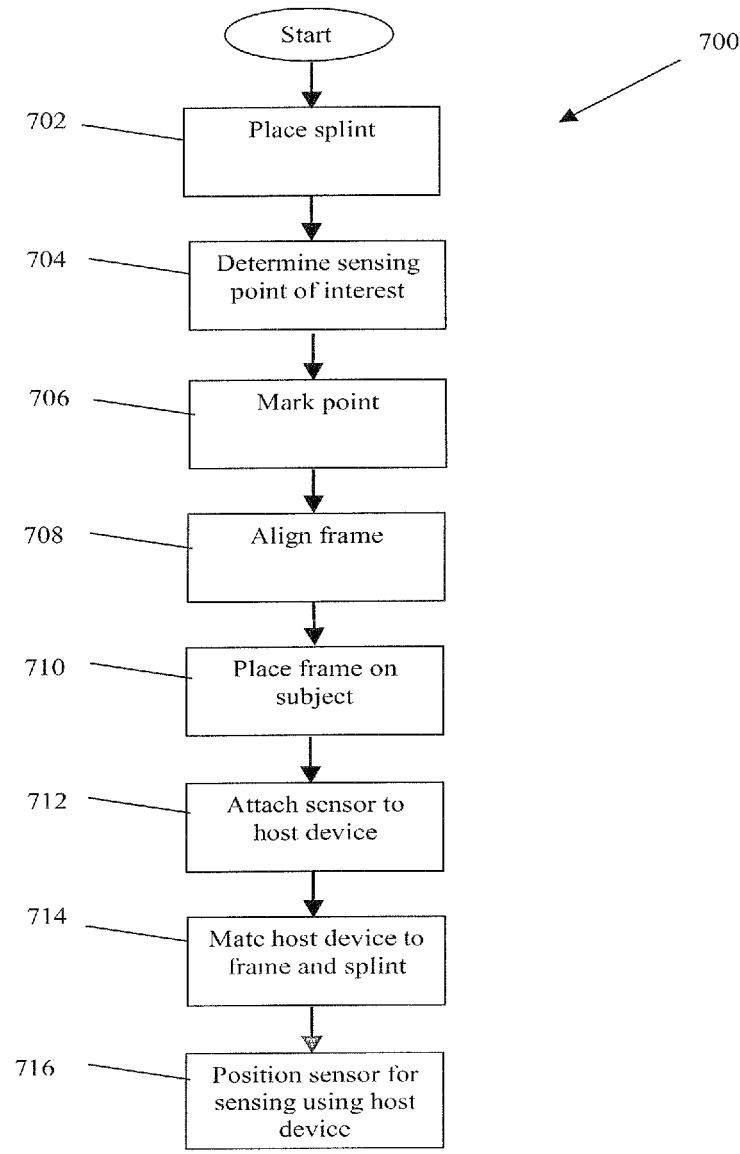
FIG. 5 is a logical flow diagram of another embodiment of the method, specifically by which the hemodynamic assessment apparatus of FIGS. 2h-2i may be used.

Referring now to FIG. 5, one embodiment of the method 700 of using the apparatus of FIGS. 2h and 2i is described. In this exemplary operational scenario, the reusable sensor 600 of FIG. 2i is used in conjunction with the limited-use frame 500 of FIG. 2h.

First, a splint of the type described in various of the foregoing co-owned applications previously incorporated herein is optionally applied to the subject per step 702. Use of the splint provides, inter alia, additional stabilization for the host device (e.g., "bracelet"), and comfort for the user.

Next, a point of interest on the living subject is identified per step 704. For example, the user may find the point of interest usual visual techniques, as well as using specially designed apparatus (such as a stethoscope), or by feel with the finger(s) such as by palpation of the radial artery. The point is marked or otherwise noted (step 706), and the frame aligned over the point of interest using the alignment apparatus (step 708).

Figure 6:
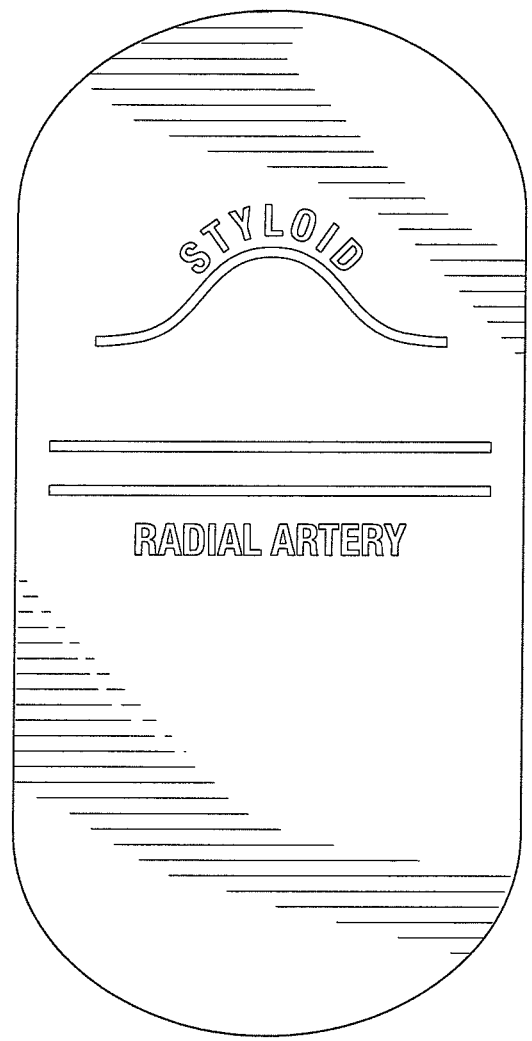
FIG. 6 is an illustration of one exemplary embodiment of the visual aid for aligning the frame on the subject.

In one variant, the point of interest is denoted by the user via a line marked onto the surface of the subject's skin. The reticle is configured so that midpoint of the line corresponds to the styloid process. FIG. 6 illustrates an exemplary visual aid (such as e.g., the membrane) which is used for alignment of the frame element. As shown, the reticle consists of 2 parallel lines, which are aligned to a mark made on the patient's wrist during application such that the line on the wrist will be disposed between the two parallel lines of the reticle. This feature therefore assists with medial/lateral alignment.

The second feature of the visual aid of FIG. 6 is a curved line intended to guide the user in the correct orientation of the frame relative to the wrist. In one embodiment, the phrase "styloid" may be printed on the visual aid as well thereby supplementing the phrase "ulnar side" printed, in one embodiment, on the frame. In this manner, the user is prevented from placing the frame 180 degrees off from its intended placement.

It is appreciated that the curved printed line may, in one variant, align approximately with the subject's radial styloid process. The edge of the frame is aligned to the subject's wrist break for proximal/distal alignment. Generally, the width of the frame is such that the midpoint of the two parallel lines (and thus the sensor) is aligned as close as possible to the radial styloid process when the edge of the frame is aligned to the subject's wrist break. However, variations in size and shape of the subject's wrist may vary this alignment slightly.

Once aligned, the frame 500 is affixed (via the adhesive side of the membrane layer 514 or other mechanism for securing) to the subject per step 710. The membrane portion 514 of the frame 500 separates the surface of the subject's skin from coming into contact with the active surface 630 of the sensor apparatus.

The sensor assembly 600 is then inserted into the host device or actuator (if not already there) per step 712. This places the circuitry/terminals 616 into contact with the interior elements of the receptacle of the actuator 300. The sensor element 600 is held securely within the actuator via the aforementioned friction/snap fit or other suitable mechanisms. The prepared host device (i.e., with actuator having the multi-use sensor assembly 600 received therein) is then secured into place on the frame 500 and splint via the risers 504, indentations 526, and lip 506 previously described (step 714).

When the host device is secured into position on the frame 500, the active surface of the sensor assembly 630 is proximate to or in contact with the membrane 516 at the point of interest (for example, at a position on the subject's skin just above the radial artery). The sensor is then manipulated by the actuator of the host device (such as by applanating the subject's tissue, and/or lateral/proximal movement of the sensor) across the membrane, in order to place the sensor in the proper position for collecting data regarding hemodynamic or other parameters of the subject (step 716). In one variant, this positioning is accomplished using a positioning algorithm running on the host device of the type described in the foregoing incorporated references, which drives the actuator motor(s) to position the sensor in three dimensions according to data received through the sensor.

When the user has completed collecting data, the frame element 500 is removed from the subject and disposed of properly. The sensor element 600 may remain held within the actuator or alternatively may be removed using the removal ring 620. A separate actuator cover may be provided if desired to protect the active surface 630 of the sensor in the instance the sensor element 600 is allowed to remain within the actuator. In this manner, the sensor 600 may be reused within the actuator for subsequent hemodynamic parameter measurements on this or another subject.

It is noted that many variations of the methods described above may be utilized consistent with the present invention. Specifically, certain steps are optional and may be performed or deleted as desired. Similarly, other steps (such as additional data sampling, processing, filtration, calibration, or mathematical analysis for example) may be added to the foregoing embodiments. Additionally, the order of performance of certain steps may be permuted, or performed in parallel (or series) if desired. Hence, the foregoing embodiments are merely illustrative of the broader methods of the invention disclosed herein.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. A physiologic parameter sensing apparatus, comprising:
   a conformal frame configured to couple to a patient's forearm comprising an alignment element comprising an optical alignment guide and a sensor barrier, said frame comprising an aperture, said sensor barrier configured to traverse said aperture;
   a host assembly comprising an actuator device configured to mate with a sensor, said host assembly being removably coupled to said frame, and said sensor being placed in communication with said sensor barrier via said host assembly coupled to said frame; and
   one or more releasable attachment features configured to facilitate removal of said host assembly from said conformal frame, whereby said removal results in a removal of said actuator and said sensor from contact with said frame and said sensor barrier;
   wherein said sensor barrier is configured to permit one or more physiologic parameters to be sensed through said sensor barrier;
   wherein said optical alignment guide is configured to facilitate placement of said frame and said sensor relative to a blood vessel of a living subject;
   wherein said sensor comprises a removal apparatus configured to configured to enable removal of said sensor from said host assembly, said removal apparatus comprising:
      a main body retained within a removal apparatus retainer of a sensor housing; and
      a user-graspable projection extended outwardly from said sensor housing configured to be pulled by a user.

2. The apparatus of claim 1, wherein said sensor barrier comprises said optical alignment guide.

3. The apparatus of claim 1, wherein a lubricant is utilized to facilitate movement of said sensor relative to said sensor barrier.

4. The apparatus of claim 3, wherein said lubricant comprises a powder.

5. The apparatus of claim 1, wherein said frame is configured to be disposed of after a single use.

6. The apparatus of claim 1, wherein said sensor comprises an electrical interface configured to directly place said sensor and said sensor actuator device in electrical communication upon said sensor being mated to said actuator device.

7. Apparatus configured to sense one or more physiologic parameters from a living subject, said apparatus comprising:
   a conformal frame configured to be disposed of after use on a single patient, and comprising an alignment element having a sensor barrier, said sensor barrier comprising a film configured to permit said one or more physiologic parameters to be sensed from a surface of skin of said living subject through said sensor barrier, said sensor barrier being coupled to said conformal frame via, at least, two regions adjacent to an aperture of said conformal frame;
   a multi-use sensor configured for use on more than one patient; and
   a host device configured to house said multi-use sensor, said host device being removably coupled to said conformal frame via one or more releasable attachment mechanisms of said host device, said host device configured to place said multi-use sensor in relative proximity to said sensor barrier;
   wherein removal of said host device from said conformal frame comprises a separation of said multi-use sensor from said conformal frame via said one or more releasable attachment mechanisms of said host device, said multi-use sensor comprising continued engagement to said host device throughout said removal; and
   wherein said sensor comprises a removal apparatus configured to configured to enable removal of said sensor from said host assembly, said removal apparatus comprising:
      a main body retained within a removal apparatus retainer of a sensor housing; and
      a user-graspable projection extended outwardly from said sensor housing configured to be pulled by a user.

8. The apparatus of claim 7, wherein said alignment element comprises a single-use adhesive surface configured to adhere said alignment element to said skin of said living subject.

9. The apparatus of claim 7, wherein said multi-use sensor comprises a pull ring configured to enable removal of said multi-use sensor from said host device when pulled by a user.

10. The apparatus of claim 7, wherein said host device comprises a bracelet-like apparatus configured to encircle a wrist of said living subject when applied.

11. The apparatus of claim 10, further comprising a support apparatus configured to be worn on an arm of said living subject;
   wherein said bracelet-like apparatus is configured to couple to said support apparatus.

12. The apparatus of claim 11, wherein said support apparatus comprises a splint.

13. A method of measuring one or more physiologic parameters of a living subject, said method comprising:
   disposing at least one frame element on said living subject, said at least one frame element comprising an aperture and a membrane, said membrane extending across said aperture, and said at least one frame element configured to be disposed of after a single use;
   mating a host device to said at least one frame element, said host device comprising an actuator device configured to mate with a sensor element, said sensor element configured to be used sequentially on multiple patients, said host device configured to be removably coupled to said at least one frame element via releasable coupling of a first securing feature of said host device to second securing feature of said at least one frame element, said act of mating comprising enabling at least an active surface of said sensor element to be disposed within said aperture of said at least one frame element, said sensor element without being indirectly coupled to said at least one frame element via said host device, while said host device is directly coupled to said at least one frame element;
   using said host device to automatically position said sensor element at a prescribed monitoring location, and calibrate said sensor element;
   measuring said one or more physiologic parameters of said living subject using said sensor element; and
   upon completion of said act of measuring, removing said host device with said sensor element coupled thereto from mating to said at least one frame element via uncoupling of said first securing feature from said second securing feature;
   wherein said act of measuring is performed through said membrane which inhibits said sensor element from contact with a surface of said living subject's skin.

14. The method of claim 13, wherein said act of using said host device to automatically position said sensor element further comprises automatically zeroing said sensor element with respect to a placement of said sensor element on said living subject.

15. The method of claim 13, further comprising coupling said sensor element to said host device, said act of coupling comprising simultaneously forming both electrical and mechanical connections between said host device and said sensor element.

16. The method of claim 13, further comprising:
mating said host device with said sensor element coupled thereto to a second frame element of a second living subject; and
obtaining measurements of said one or more physiologic parameters of said second living subject.

17. The apparatus of claim 7, wherein:
said host device with said multi-use sensor coupled thereto is further configured to mate to a second conformal frame of a second living subject; and
said multi-use sensor is further configured to obtain measurements of said one or more physiologic parameters of said second living subject.

18. The apparatus of claim 1, wherein said one or more releasable attachment features comprise a first securing feature of said host assembly and a second securing feature of said frame.

19. The apparatus of claim 18, wherein said first securing feature comprises at least one projection and said second securing feature comprises at least one riser having at least one indentation configured to receive said at least one projection.

20. The apparatus of claim 1, wherein said sensor is indirectly coupled to said frame while said host assembly is directly coupled to said frame.

21. The apparatus of claim 7, wherein said one or more releasable attachment mechanisms comprise a first securing feature of said host device and a second securing feature of said conformal frame.

22. The apparatus of claim 21, wherein said first securing feature comprises at least one projection and said second securing feature comprises at least one riser having at least one indentation configured to receive said at least one projection.

23. The apparatus of claim 7, wherein said sensor is indirectly coupled to said frame while said host assembly is directly coupled to said frame.

24. The method of claim 13, further comprising removing said sensor element via a removal apparatus attached to said sensor element.

25. The method of claim 24, wherein said act of removing said sensor element comprises pulling on a user-graspable portion of said removal apparatus, said user-graspable portion being outwardly projected from a housing of said sensor element.

26. The method of claim 13, wherein said act of removing said host device with said sensor element coupled thereto from mating to said at least one frame element comprises release of a projection of said first securing feature from an indentation of said second securing feature.

* * * * *